(12) United States Patent
Kakinoki

(10) Patent No.: US 11,207,514 B2
(45) Date of Patent: Dec. 28, 2021

(54) MALE CONNECTOR, MEDICAL DEVICE, AND CONNECTION METHOD

(71) Applicant: TERUMO KABUSHIKI KAISHA, Tokyo (JP)

(72) Inventor: Toshihiko Kakinoki, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 181 days.

(21) Appl. No.: 16/285,111

(22) Filed: Feb. 25, 2019

(65) Prior Publication Data

US 2019/0184152 A1  Jun. 20, 2019

Related U.S. Application Data

(63) Continuation of application No. PCT/JP2017/034755, filed on Sep. 26, 2017.

(30) Foreign Application Priority Data

Sep. 26, 2016  (JP) .............................. JP2016-187372

(51) Int. Cl.
*A61M 39/10*  (2006.01)
*A61M 39/26*  (2006.01)
*A61J 1/20*  (2006.01)

(52) U.S. Cl.
CPC ........ *A61M 39/1011* (2013.01); *A61M 39/10* (2013.01); *A61M 39/26* (2013.01);
(Continued)

(58) Field of Classification Search
CPC ............ A61M 39/26; A61M 2039/267; A61M 39/1011; A61M 2039/1033;
(Continued)

(56) References Cited

U.S. PATENT DOCUMENTS 5,492,147 A * 2/1996 Challender ........... F16L 29/005
137/614.05
8,157,784 B2  4/2012 Rogers
(Continued)

FOREIGN PATENT DOCUMENTS

CN  1919368 A  2/2007
CN  101111282 A  1/2008
(Continued)

OTHER PUBLICATIONS

Extended European Search Report dated Feb. 17, 2020 for corresponding European Patent Application No. 17853232.
(Continued)

*Primary Examiner* — Emily L Schmidt
(74) *Attorney, Agent, or Firm* — Foley & Lardner LLP

(57) ABSTRACT

A male connector is connectable to a female connector and includes: a flow path tubular member that has an opening at an end portion; a valve body that closes the opening; a housing main body; and a moving body that moves with respect to the housing main body and deforms the valve body so as to change a mode between a first mode in which the opening is closed by the valve body and a second mode in which the opening is open from the valve body. The moving body includes a locking portion that locks the female connector in a state in which the valve body and an elastic valve body of the female connector abut on each other.

14 Claims, 15 Drawing Sheets

(52) U.S. Cl.
CPC ..... *A61J 1/2089* (2013.01); *A61M 2039/1033* (2013.01); *A61M 2039/268* (2013.01)

(58) Field of Classification Search
CPC .. A61M 2039/1072; A61M 2039/1038; A61M 2039/2486
See application file for complete search history.

(56) References Cited

U.S. PATENT DOCUMENTS

| | | | |
|---|---|---|---|
| 2006/0142735 | A1 | 6/2006 | Whitley |
| 2011/0106046 | A1* | 5/2011 | Hiranuma ............. A61J 1/2096 604/414 |
| 2011/0276035 | A1* | 11/2011 | Fangrow, Jr. ......... A61M 39/26 604/535 |
| 2012/0157914 | A1 | 6/2012 | Stroup |
| 2018/0000695 | A1* | 1/2018 | Stroup ............... A61M 5/14228 |
| 2019/0275316 | A1* | 9/2019 | Stjernberg Bejhed ....................... A61M 39/1011 |

FOREIGN PATENT DOCUMENTS

| | | |
|---|---|---|
| CN | 101980746 A | 2/2011 |
| CN | 104394925 A | 3/2015 |
| EP | 1 946 792 A1 | 7/2008 |
| EP | 2 428 248 A1 | 3/2012 |
| JP | 2002-526179 A | 8/2002 |
| JP | 2012-254142 A | 12/2012 |

OTHER PUBLICATIONS

International Searching Authority, "International Search Report," issued in connection with International Patent Application No. PCT/JP2017/034755, dated Jan. 9, 2018.

International Searching Authority, "Written Opinion," issued in connection with International Patent Application No. PCT/JP2017/034755, dated Jan. 9, 2018.

Office Action dated Nov. 30, 2020 in corresponding Chinese Patent Application No. 201780057871.9.

* cited by examiner

MALE CONNECTOR, MEDICAL DEVICE, AND CONNECTION METHOD

CROSS-REFERENCE TO RELATED APPLICATIONS

This is a bypass continuation of PCT Application No. PCT/JP2017/034755, filed on Sep. 26, 2017, which claims priority to Japanese Application No. 2016-187372, filed on Sep. 26, 2016. The contents of these applications are hereby incorporated by reference in their entireties.

BACKGROUND

The present disclosure relates to a male connector, a medical device including a male connector, and a method of connecting a male connector and a female connector.

When performing infusion to a patient, it is necessary to form a route (infusion line) configured to transport a fluid, such as a medicinal solution. The infusion line is generally formed by connecting an infusion tube and various medical devices. Further, it is necessary to connect a medicinal solution bag and a syringe or the like when injecting a fluid such as a medicinal solution to be administered to a patient into the medicinal solution bag. In this manner, a male connector and a female connector are used to connect different members to each other in a detachable manner.

Among the medicinal solutions, there is a medicinal solution containing a drug designated as a powerful drug, such as an anticancer agent, and a medical operator needs to pay sufficient attention so as to inhibit a fluid such as dangerous medicinal solution from adhering to a finger and the like when attaching and detaching the male connector or the female connector.

U.S. Pat. No. 8,157,784 discloses a transfer system (male connector) that includes: a housing that defines a hollow portion; a first moving membrane (valve body) that is arranged at a distal end of the hollow portion and seals the housing; a cannula extending in the hollow portion; and a biasing portion that biases the moving membrane toward the distal end within the hollow portion. A tip (distal end) of the cannula is positioned within a slit of the first moving membrane in a natural state. According to the disclosure of U.S. Pat. No. 8,157,784, when the first moving membrane is pushed from a distal end side to a proximal end side by a second moving membrane (valve body) of a receiver device (female connector), the tip of the cannula passes through the slit and penetrates the second moving membrane to communicate with the housing of the receiver device while inhibiting an outflow of a fluid (medicinal solution) from the tip of the cannula in a state in which the first moving membrane and the second moving membrane are in contact with each other.

SUMMARY

However, when the female connector is quickly removed from the male connector described in U.S. Pat. No. 8,157,784, for example, there is a problem that the first moving membrane and the second moving membrane are separated from each other before the tip of the cannula returns to the inside of the slit of the first moving membrane so that there is a risk that the fluid may leak from the tip of the cannula to the outside.

In view of the above problem, one object of certain embodiments of the present disclosure is to provide a male connector, a medical device including the male connector, and a method of connecting the male connector and a female connector that are capable of inhibiting a fluid such as a medicinal solution from leaking to the outside when removing the connected female connector.

According to one embodiment, a male connector is connectable to a female connector having an elastic valve body, and includes: a housing that defines a hollow portion; a flow path tubular member that extends inside the hollow portion and has an opening at one end portion in an extending direction; and a valve body that is positioned inside the hollow portion and closes the opening of the flow path tubular member. The housing includes: a housing main body; and a moving body that moves with respect to the housing main body and deforms or moves the valve body so as to change a mode between a first mode in which the opening of the flow path tubular member is closed by the valve body and a second mode in which the opening of the flow path tubular member is open from the valve body. The moving body includes a locking portion that locks the female connector in a state in which the valve body and the elastic valve body of the female connector abut on each other to form an abutment region. At least any one of the housing main body and the moving body includes a switching portion that is displaceable between a restriction position to restrict movement of the other of the housing main body and the moving body so as to maintain the first mode and an allowing position to allow the movement of the other so as to change from the first mode to the second mode while maintaining a state in which the locking portion locks the female connector.

According to one aspect of the present invention, when the locking portion is set as a first locking portion, the switching portion includes a second locking portion that locks the other at the restriction position such that a mode is changeable between the first mode and the second mode by switching between locking and unlocking of the other performed by the second locking portion.

According to one aspect of the present invention, the second locking portion includes a convex portion that fits in a concave portion provided on the other.

According to one aspect of the present invention, a female screw portion is formed on an inner peripheral wall of the housing main body, and the moving body moves with respect to the housing main body as a male screw portion formed on an outer peripheral wall of the moving body is screwed with the female screw portion.

According to one aspect of the present invention, when the male screw portion is set as a first male screw portion and the female screw portion is set as a first female screw portion, the second female screw portion is formed on an inner peripheral wall of the moving body, the second male screw portion, screwable with the second female screw portion, is formed on an outer peripheral wall of the female connector, and the first locking portion includes the second female screw portion.

According to one aspect of the present invention, a direction in which the moving body moves by screwing between the first male screw portion and the first female screw portion as the moving body rotates in a predetermined direction with respect to the housing main body is identical to a direction in which the female connector moves by screwing between the second male screw portion and the second female screw portion as the female connector rotates in the predetermined direction with respect to the moving body.

According to one aspect of the present invention, the valve body biases the moving body in the second mode to be in the first mode by a restoring force.

According to one aspect of the present invention, the valve body covers the one end portion including the opening of the flow path tubular member, and the flow path tubular member does not pass through the valve body in the first mode, and the flow path tubular member passes through the valve body in the second mode According to another embodiment of the present invention, a male connector is connectable to a female connector having an elastic valve body, and includes: a housing that defines a hollow portion; a flow path tubular member that extends inside the hollow portion and has an opening at one end portion in an extending direction; and a valve body that is positioned inside the hollow portion and closes the opening of the flow path tubular member. The housing includes: a housing main body; and a moving body that moves with respect to the housing main body and deforms or moves the valve body so as to change a mode between a first mode in which the opening of the flow path tubular member is closed by the valve body and a second mode in which the opening of the flow path tubular member is open from the valve body. The moving body is moved so as to change from the first mode to the second mode in a state in which the valve body and the elastic valve body of the female connector abut on each other to form an abutment region in the first mode so that the flow path tubular member is caused to pass through the valve body and the elastic valve body through the abutment region.

According to one embodiment of the present invention, a male connector is connectable to a female connector having an elastic valve body, and includes: a housing that defines a hollow portion; a flow path tubular member that extends inside the hollow portion and has an opening at one end portion in an extending direction; and a valve body that is positioned inside the hollow portion and closes the opening of the flow path tubular member. The housing includes: a housing main body; and a moving body that moves with respect to the housing main body and deforms or moves the valve body so as to change a mode between a first mode in which the opening of the flow path tubular member is closed by the valve body and a second mode in which the opening of the flow path tubular member is open from the valve body. The moving body is moved so as to change from the second mode to the first mode in a state in which the valve body and the elastic valve body of the female connector abut on each other to form an abutment region in the second mode so that the flow path tubular member is caused to be removed from the elastic valve body through the abutment region.

According to another embodiment of the present invention, a medical device includes the male connector.

According to another embodiment of the present invention, a connection method for connecting a female connector including an elastic valve body and a male connector is provided. The male connector includes: a housing that defines a hollow portion; a flow path tubular member that extends inside the hollow portion and has an opening at one end portion in an extending direction; and a valve body that is positioned inside the hollow portion and closes the opening of the flow path tubular member, the housing including: a housing main body; and a moving body that moves with respect to the housing main body and deforms or moves the valve body so as to change a mode between a first mode in which the opening of the flow path tubular member is closed by the valve body and a second mode in which the opening of the flow path tubular member is open from the valve body. The method includes: locking the female connector by the moving body in a state in which the valve body and the elastic valve body of the female connector abut on each other to form an abutment region in the first mode; and moving the moving body so as to change from the first mode to the second mode in a state in which the female connector is locked by the moving body so that the flow path tubular member is caused to pass through the valve body and the elastic valve body through the abutment region.

According to the male connector, the medical device including the male connector, and the method of connecting the male connector and the female connector of the present disclosure, it is possible to inhibit the fluid such as the medicinal solution from leaking to the outside when removing the connected female connector.

DETAILED DESCRIPTION

Hereinafter, a medical device according to embodiments of the invention will be described with reference to the drawings. Common members are denoted by identical reference signs throughout the drawings.

First Embodiment

Figure 1:
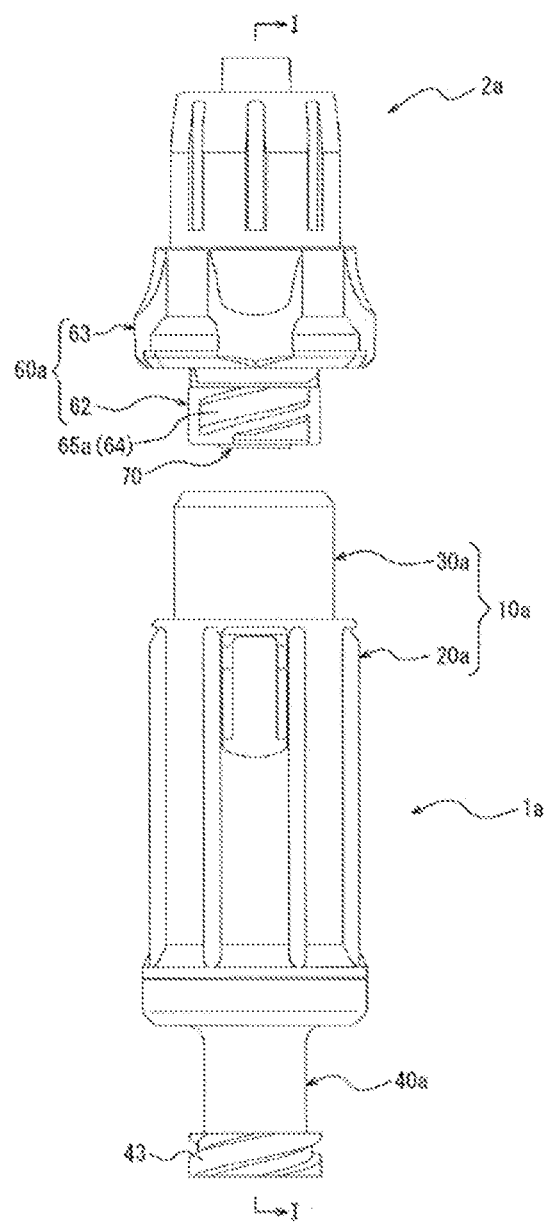
FIG. 1 is a side view illustrating a male connector and a female connector according to a first embodiment.
Figure 2:
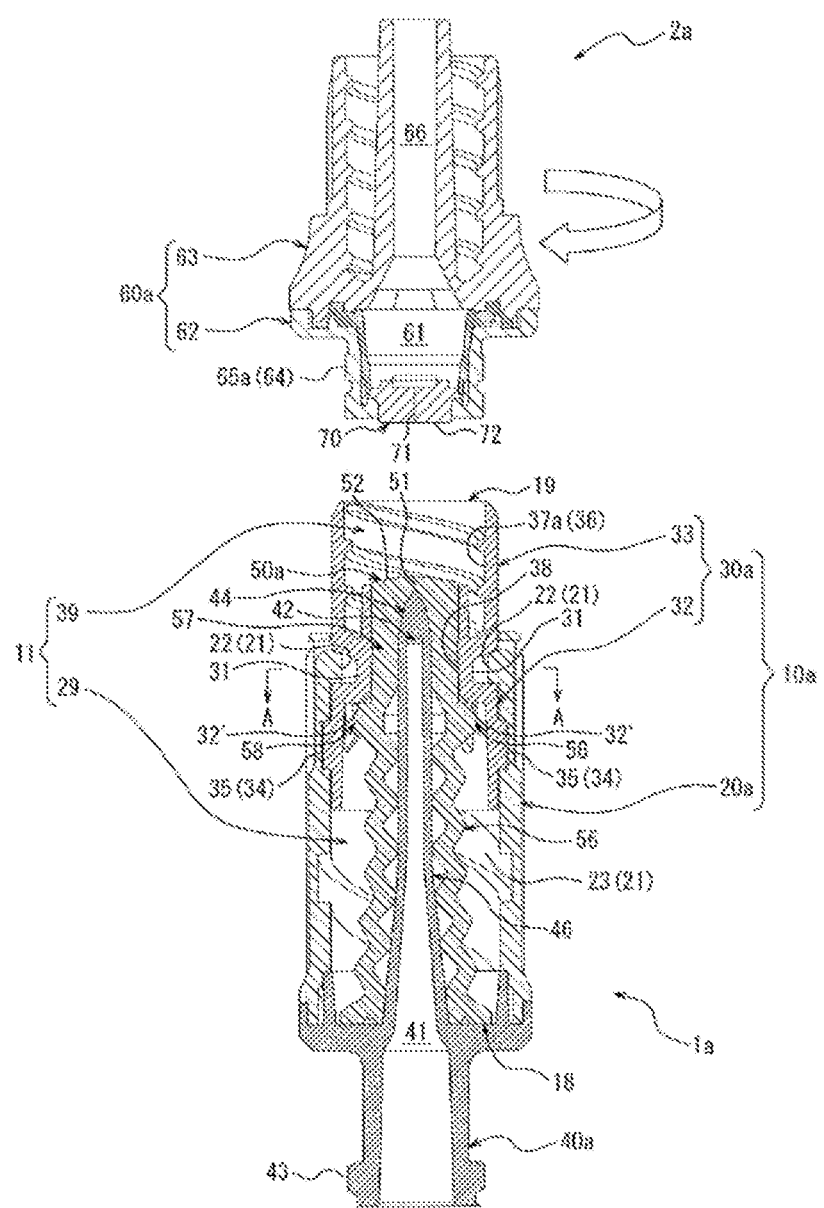
FIG. 2 is a cross-sectional view taken along line I-I of FIG. 1.

FIG. 1 is a side view illustrating a male connector 1a and a female connector 2a according to a first embodiment, and FIG. 2 is a cross-sectional view taken along line I-I of FIG. 1. The male connector 1a and the female connector 2a illustrated in FIGS. 1 and 2 illustrate states as each single body before being connected to each other (non-connection state). Hereinafter, in the male connector and the female connector according to each embodiment, one end side, which is the downstream side (upper side in FIG. 1) of a flow path of a fluid such as a medicinal solution in an infusion line, will be referred to as a "distal end" side, and the other end side, which is the upstream side (lower side in FIG. 1) of the flow path of the fluid in the infusion line, will be referred to as a "proximal end" side.

As illustrated in FIGS. 1 and 2, the male connector 1a includes a housing 10a, a flow path tubular member 40a, and a valve body 50a. The housing 10a defines a hollow portion 11, the flow path tubular member 40a extends inside the hollow portion 11 and has an opening 42 at one end portion on the distal end side in an extending direction, and the valve body 50a is positioned inside the hollow portion 11 and covers the one end portion on the distal end side in the extending direction of the flow path tubular member 40a to close the opening 42.

Further, the female connector 2a includes a housing 60a and an elastic valve body 70 as illustrated in FIGS. 1 and 2. The housing 60a defines a male connector insertion portion 61 and a flow path 66 as hollow portions, the elastic valve body 70 is positioned at a proximal end of the housing 60a, and has a top surface facing the male connector insertion portion 61 and a bottom surface facing the outside of the female connector 2a.

Hereinafter, configurations of the male connector 1a and the female connector 2a will be described in detail. The housing 10a of the male connector 1a will be referred to as a "first housing 10a", and the housing 60a of the female connector 2a will referred to as a "second housing 60a" for convenience of description. Further, the flow path 41 of the male connector 1a will be referred to as a "first flow path 41", and the flow path 66 of the female connector 2a will referred to as a "second flow path 66" for convenience of description.

<Male Connector 1a>

The first housing 10a includes a housing main body 20a and a moving body 30a movable with respect to the housing main body 20a. The hollow portion 11 of the first housing 10a is constituted by a hollow portion 29 defined by the housing main body 20a and a hollow portion 39 defined by the moving body 30a.

The housing main body 20a is a tubular member extending from the proximal end side to the distal end side with one end on the proximal end side forming a proximal end 18 of the first housing 10a. A first female screw portion 23 is formed on an inner peripheral wall 21 of the housing main body 20a. Further, claw-shaped convex portions 22 protruding inward are provided on the inner peripheral wall 21 of the housing main body 20a. An end surface on the distal end side of the convex portion 22 is inclined so as to be directed toward the proximal end side in the radially inward direction. On the other hand, an end surface on the proximal end side of the convex portion 22 is substantially parallel to the radial direction.

The moving body 30a is a tubular member extending from the proximal end side to the distal end side, and has a proximal-end-side tubular portion 32 at the proximal end side and a distal-end-side tubular portion 33 at the distal end side. One end on the distal end side of the distal-end-side tubular portion 33 forms a distal end 19 of the first housing 10a. A first male screw portion 35 is formed on an outer peripheral wall (proximal-end-side outer peripheral wall) 34 of the proximal-end-side tubular portion 32. As the first male screw portion 35 is screwed with the first female screw portion 23 formed on the inner peripheral wall 21 of the housing main body 20a, the moving body 30a is movable toward the proximal end side and the distal end side with respect to the housing main body 20a. In this example, the moving body 30a moves to the proximal end side as the moving body 30a rotates clockwise with respect to the housing main body 20a to screw the first male screw portion 35 and the first female screw portion 23, and moves to the distal end side by rotating counterclockwise with respect to the housing main body 20a. Further, a second female screw portion 37a that can be screwed with a second male screw portion 65a formed in the female connector 2a to be described below is formed on an inner peripheral wall (distal-end-side inner peripheral wall) 36 of the distal-end-side tubular portion 33.

Figure 3:
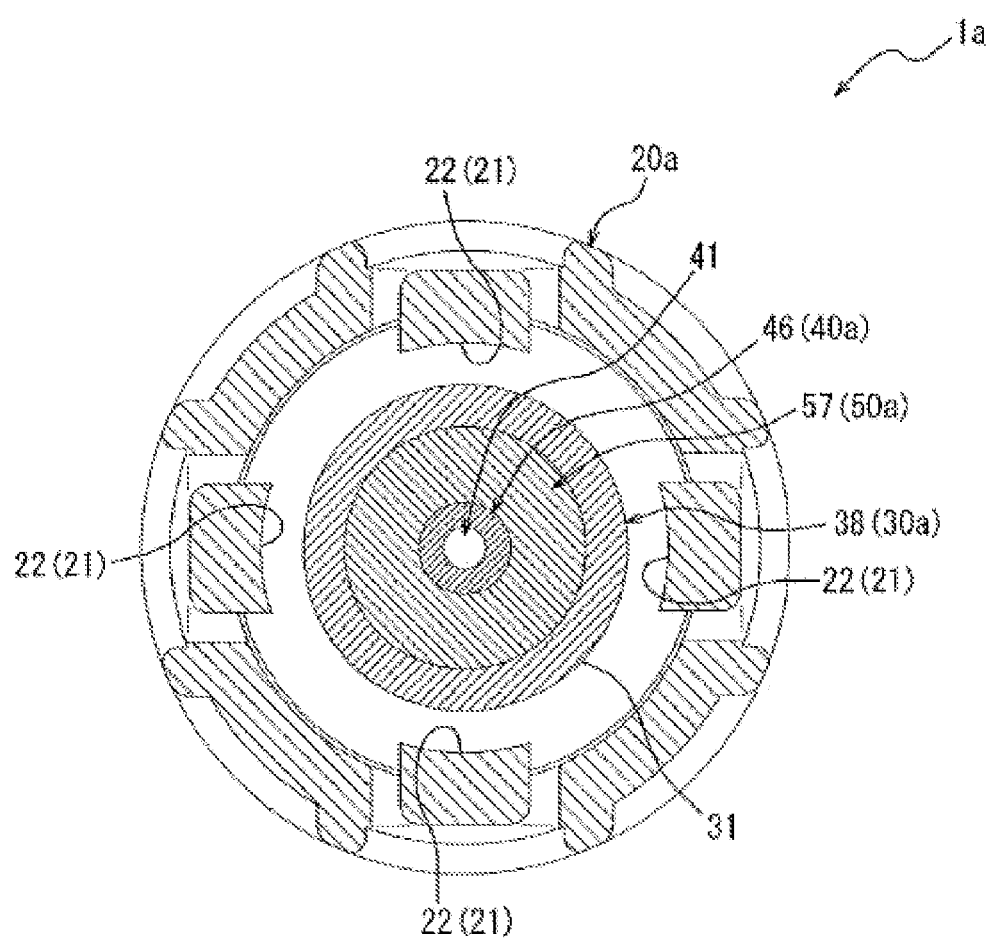
FIG. 3 is a cross-sectional view taken along line A-A of FIG. 2.

The moving body 30a is provided with a concave portion 31 on the outer peripheral wall between the proximal-end-side tubular portion 32 and the distal-end-side tubular portion 33. As the convex portion 22 serving as a second locking portion provided on the inner peripheral wall 21 of the housing main body 20a is fitted and locked in the concave portion 31, the movement of the moving body 30a is restricted so as to maintain a mode (hereinafter referred to as a "first mode") in which the flow path tubular member 40a does not pass through the valve body 50a and the opening 42 of the flow path tubular member 40a is closed by the valve body 50a as illustrated in FIG. 2. Hereinafter, a position of the convex portion 22 at the time of restricting the movement of the moving body 30a so as to maintain the first mode, that is, the position of the convex portion 22 that has been fitted and locked in the concave portion 31 will be referred to as a restriction position. In this example, the four convex portions 22 provided at substantially equal intervals along the circumferential direction of the inner peripheral wall 21 of the housing main body 20a are fitted into an annular groove serving as the concave portion 31 continuously provided over the entire circumference of the outer peripheral wall of the moving body 30a as illustrated in FIG. 3 as a cross-sectional view taken along line A-A of FIG. 2.

Further, the moving body 30a includes a tubular valve body holding portion 38 that internally holds the end portion on the distal end side of the valve body 50a. The valve body holding portion 38 is provided inside the distal-end-side tubular portion 33. Further, a stepped surface 32' facing the proximal end side is formed on an inner wall of the proximal-end-side tubular portion 32. When the moving body 30a moves toward the proximal end side with respect to the housing main body 20a, the valve body 50a is compressed and deformed toward the proximal end side by being pressed against the stepped surface 32' of the moving body 30a.

Examples of materials for the housing main body 20a and the moving body 30a, which form the first housing 10a, include various resin materials such as polyolefin such as polyethylene, polypropylene, and an ethylene-propylene copolymer; an ethylene-vinyl acetate copolymer (EVA); polyvinyl chloride; polyvinylidene chloride; polystyrene; polyamide; polyimide; polyamide-imide; polycarbonate; poly(4-methylpentene-1); ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), and polycyclohexane terephthalate (PCT); polyether; polyether ketone (PEK); polyether ether ketone (PEEK); polyether imide; polyacetal (POM); polyphenylene oxide; modified polyphenylene oxide; polysulfone; polyether sulfone; polyphenylene sulfide; polyarylate; aromatic polyester (a liquid crystal polymer); and polytetrafluoroethylene, polyvinylidene fluoride, and other fluororesins. Further, a blend or a polymer alloy containing one or more kinds of the above materials may also be used. Alternatively, various glass materials, ceramic materials, or metal materials may be used.

The flow path tubular member 40a defines a first flow path 41 therein, and the first flow path 41 communicates with the outside through the opening 42. The flow path tubular member 40a is connected with the housing main body 20a at the proximal end 18 of the first housing 10a to seal the proximal end side of the hollow portion 29 of the housing main body 20a. The flow path tubular member 40a includes a medical device connection portion 43 connectable to a medical device such as a medical tube at an end portion on the proximal end side. Further, the flow path tubular member 40a includes a flow path tube main body 46 extending into the hollow portion 11 of the first housing 10a and having the opening 42 formed at the distal end portion. The first flow path 41 communicates from the proximal end of the medical device connection portion 43 to the opening 42 at the distal end portion of the flow path tube main body 46. Further, the flow path tubular member 40a includes a tip portion 44, which is reduced in diameter toward the distal end side in the extending direction of the flow path tubular member 40a, at the end portion on the distal end side. In the present embodiment, the tip portion 44 is formed in a shape including two tapered portions having different diameter reduction ratios, but may be a semi-spindle shape or a conical shape.

The flow path tubular member 40a can be formed of the same material as the above-described first housing 10a.

The valve body 50a covers the flow path tube main body 46 inside the first housing 10a. Specifically, the valve body 50a of the present embodiment has a bellows-cylindrical portion 56 elastically deformable toward the distal end side and the proximal end side and a tip portion 57 continuous with the bellows-cylindrical portion 56 so as to close the distal end side of a hollow portion of the bellows-cylindrical portion 56 and held by the valve body holding portion 38 of the moving body 30a. An end portion on the proximal end side of the bellows-cylindrical portion 56 is in contact with the flow path tubular member 40a. The tip portion 57 is held by the valve body holding portion 38 of the moving body 30a. Specifically, an annular flange portion 58 protruding radially outward is formed between the bellows-cylindrical portion 56 and the tip portion 57 of the valve body 50a, and the annular flange portion 58 abuts on the above-described stepped surface 32' of the moving body 30a so that it is possible to maintain a state in which the tip portion 57 does not protrude from the distal end of the valve body holding portion 38 but is accommodated in the valve body holding portion 38. Further, a slit 51 penetrating from the proximal end side to the distal end side is formed in the tip portion 57, and a top surface 52 that is an end surface on the distal end side has a convex curved surface and is exposed to the outside from the valve body holding portion 38. Although the entire top surface 52 forms the convex curved surface in the present embodiment, a convex curved surface may be formed only around the slit 51. The top surface 52 has the convex curved surface, and thus, is likely to come into close contact with a bottom surface 72 of the elastic valve body 70 of the female connector 2a to be described below so that it is possible to more reliably inhibit a fluid such as a medicinal solution from leaking to the outside when the connected female connector 2a is removed. Further, in the first embodiment illustrated in FIG. 2, the end portion on the distal end side including the opening 42 of the flow path tubular member 40a is covered by the valve body 50a, whereby the opening 42 is closed. A hardness of the valve body 50a is preferably a Shore A hardness of between 10 and 70, and more preferably a Shore A hardness of between 20 and 50. When the hardness is less than a Shore A hardness of 10, there is a risk that a fluid such as a medicinal solution may leak out to the outside when the pressure in the first flow path 41 increases. When the hardness is larger than a Shore A hardness of 70, the abutment between the valve body 50a and the elastic valve body 70 of the connected female connector 2a becomes insufficient so that there is a risk that a fluid such as a medicinal solution may leak out to the outside when the connected female connector 2a is removed. Further, when the hardness of the valve body 50a is a Shore A hardness of between 20 and 50, it is possible to secure favorable adhesiveness with the female connector 2a, and it is possible to more reliably inhibit a fluid such as a medicinal solution from leaking out to the outside when the connected female connector 2a is removed.

The valve body 50a is molded and formed to be elastically deformable. Examples of the material of the valve body 50a include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluoro rubber; and various thermoplastic elastomers such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a transpolyisoprene-based thermoplastic elastomer, a fluoro rubber-based thermoplastic elastomer, and a chlorinated polyethylene-based thermoplastic elastomer, and a material mixed with one or two or more kinds of these materials may be used. The valve bodies 50a may be made of different materials or may be formed of the same material.

<Female Connector 2a>

The second housing 60a includes a cap 62 that defines the male connector insertion portion 61 into which the male connector 1a is inserted from the outside and a holder 63 supporting the cap 62 and defining the second flow path 66. The male connector insertion portion 61 is a hollow portion defined by the cap 62 and the holder 63, the second flow path 66 is a hollow portion defined by the holder 63, and the male connector insertion portion 61 is defined on the proximal end side relative to the second flow path 66. The hollow portion defined by the second housing 60a is constituted by the male connector insertion portion 61 and the second flow path 66.

The second male screw portion 65a, which can be screwed with the second female screw portion 37a formed in the distal end inner peripheral wall 36 of the moving body 30a, is formed on an outer peripheral wall 64 of the cap 62. In this example, the female connector 2a moves to the proximal end side by screwing between the second male screw portion 65a and the second female screw portion 37a as the female connector 2a rotates clockwise with respect to the moving body 30a, and moves to the distal end side by rotating counterclockwise with respect to the moving body 30a. That is, a direction in which the moving body 30a moves by screwing between the first male screw portion 35 and the first female screw portion 23 as the moving body 30a rotates in a predetermined direction (clockwise or counterclockwise) with respect to the housing main body 20a and a direction in which the female connector 2a moves by screwing between the second male screw portion 65a and the second female screw portion 37a as the female connector 2a rotates in a predetermined direction with respect to the moving body 30a are the same. The second housing 60a can be formed of the same material as the first housing 10a of the male connector 1a described above.

A slit 71 penetrating from the proximal end side to the distal end side is formed in the elastic valve body 70. The bottom surface 72 of the elastic valve body 70 is exposed to the outside from the proximal end side. The elastic valve body 70 can be formed of the same material as the valve body 50a of the male connector 1a described above. A hardness of the elastic valve body 70 is preferably a Shore A hardness of between 20 and 60. Further, the hardness of the elastic valve body 70 is preferably higher than the hardness of the valve body 50a of the male connector 1a. It is easy to suppress the deformation amount of the elastic valve body 70 at the time of connecting the male connector 1a and the female connector 2a while inhibiting a fluid such as a medicinal solution from leaking out to the outside when the pressure in the second flow path 66 increases by making the hardness of the elastic valve body 70 larger than the hardness of the valve body 50a. When the deformation amount of the elastic valve body 70 is large, there is a risk that a negative pressure is generated in the second flow path 66 and blood is suctioned from a blood vessel of a patient communicating with the second flow path 66 when the male connector 1a is removed from the female connector 2a.

Figure 4:
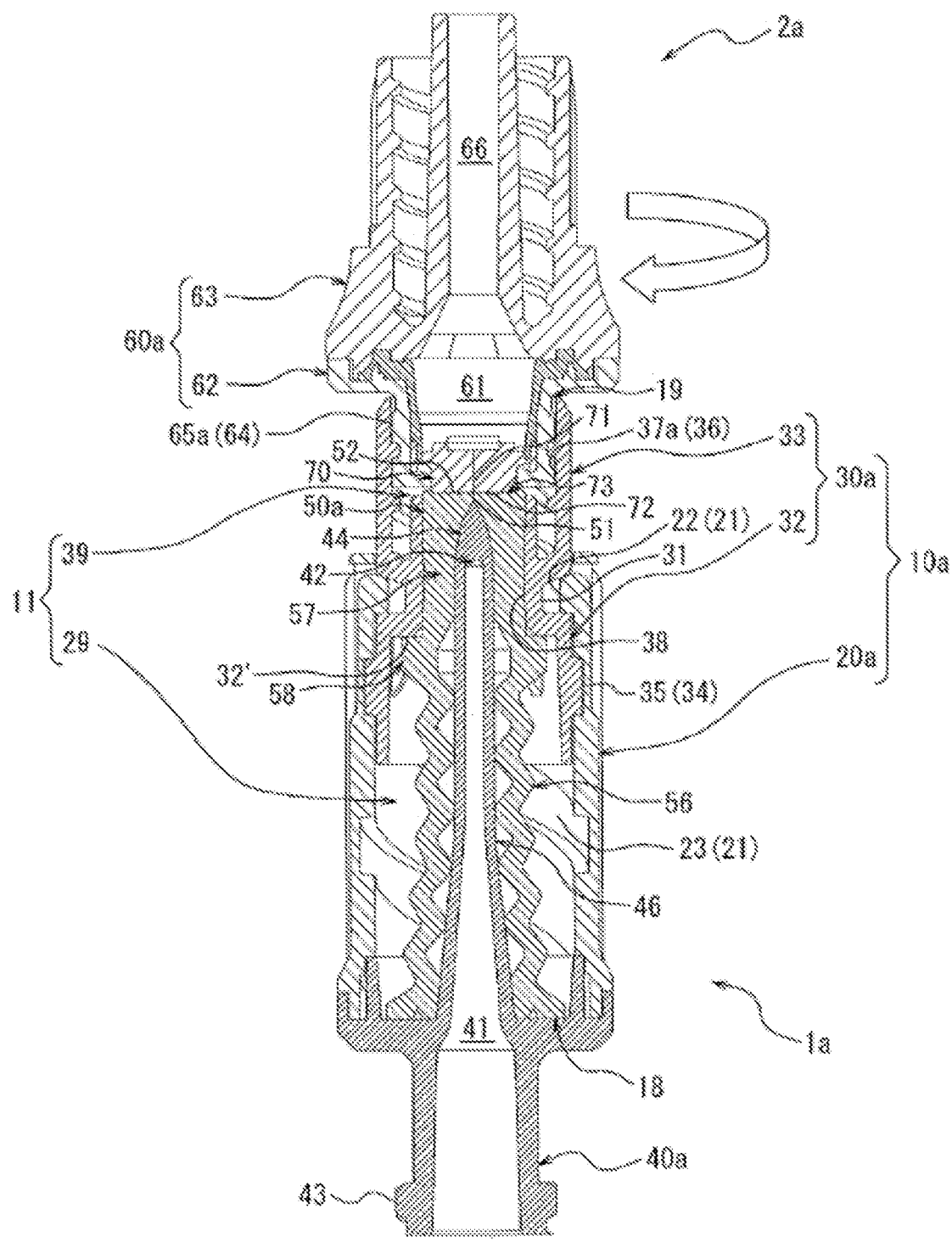
FIG. 4 is a cross-sectional view illustrating a first connection state of the male connector and the female connector illustrated in FIG. 1.
Figure 5:
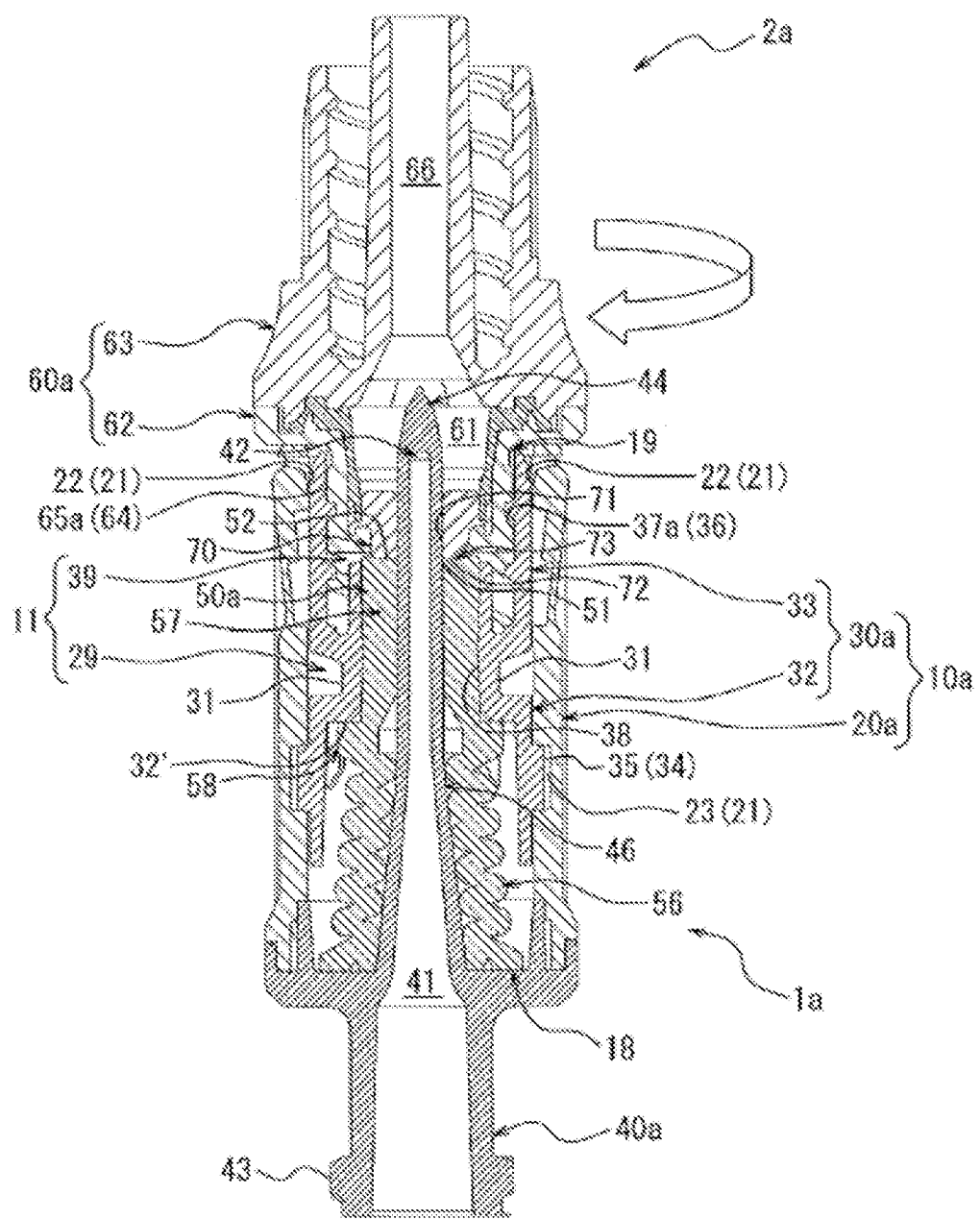
FIG. 5 is a cross-sectional view illustrating a second connection state of the male connector and the female connector illustrated in FIG. 1.

Hereinafter, a procedure of connecting the male connector 1a and the female connector 2a will be described with reference to FIGS. 2, 4, and 5. FIG. 4 is a cross-sectional view illustrating a first connection state of the male connector 1a and the female connector 2a, and FIG. 5 is a cross-sectional view illustrating a second connection state of the male connector 1a and the female connector 2a. The outlined arrows in FIGS. 2, 4, and 5 indicate a direction in which the female connector 2a is rotated with respect to the male connector 1a when connecting the female connector 2a to the male connector 1a. Details of the first connection state and the second connection state will be described below.

As illustrated in FIG. 2, in a state in which the convex portion 22 serving as the second locking portion of the housing main body 20a is fitted and locked in the concave portion 31 of the moving body 30a, that is, in the state of being at the restriction position, the female connector 2a is rotated clockwise with respect to the male connector 1a while bringing the proximal end side of the female connector 2a close to the distal end side of the male connector 1a with respect to the male connector 1a kept in the first mode. Then, the second male screw portion 65a of the female connector 2a and the second female screw portion 37a of the male connector 1a are screwed with each other so that the female connector 2a moves relative to the proximal end side with respect to the male connector 1a, and the bottom surface 72 of the elastic valve body 70 of the female connector 2a abuts on the top surface 52 of the valve body 50a of the male connector 1a to form an abutment region 73, as illustrated in FIG. 4. It is unnecessary for the abutment region 73 to be formed such that the bottom surface 72 of the elastic valve body 70 and the top surface 52 of the valve body 50a abut on each other on the entire surface. Rather, at least portions of both the bottom surface 72 and the top surface 52 through which the flow path tubular member 40a passes may abut on each other. In the present embodiment, the periphery of the slit 71 of the elastic valve body 70 and the periphery of the slit 51 of the valve body 50a may abut on each other at least to form the abutment region 73. At this time, the second male screw portion 65a of the female connector 2a and the second female screw portion 37a of the male connector 1a are screwed with each other so that the female connector 2a is locked with respect to the male connector 1a. In other words, the second female screw portion 37a of the male connector 1a is screwed with the second male screw portion 65a to form the first locking portion locking the female connector 2a. At this time, the convex portion 22 serving as the second locking portion maintains the fitting state (locking state) with the concave portion 31 at the restriction position. Hereinafter, the connection state of the male connector 1a and the female connector 2a as illustrated in FIG. 4 will be described as the "first connection state". In this example, the distal end 19 of the moving body 30a is in the state of abutting on the cap 62 of the female connector 2a in the first connection state. In the first connection state, the distal end of the valve body holding portion 38 may be in the state of abutting on the cap 62 of the female connector 2a instead of causing the distal end 19 of the moving body 30a to abut on the cap 62 of the female connector 2a.

In the first connection state illustrated in FIG. 4, the female connector 2a is further rotated clockwise with respect to the male connector 1a. Then, since the distal end 19 of the moving body 30a is in the state of abutting on the cap 62 of the female connector 2a, the moving body 30a tries to rotate clockwise with respect to the housing main body 20a together with the female connector 2a. Therefore, the fitting state between the convex portion 22 and the concave portion 31 is released. In other words, the convex portion 22 serving as the second locking portion is displaced from the restriction position to restrict the movement by locking the moving body 30a to an allowing position where the locking of the moving body 30a is released to allow the movement, while being kept in a state in which the second female screw portion 37a serving as the first locking portion maintains the abutment region 73 and locks the female connector 2a. More specifically, as described above, the convex portion 22 is displaced to the allowing position by being pushed radially outward by the moving body 30a that tries to advance toward the proximal end side since the end surface on the distal end side is inclined so as to be directed toward the proximal end side in the radially inward direction.

When the female connector 2a is further rotated clockwise with respect to the male connector 1a after the convex portion 22 has been displaced to the allowing position, the moving body 30a moves relative to the proximal end side with respect to the housing main body 20a together with the female connector 2a by changing the screwing state between the first male screw portion 35 and the first female screw portion 23. As a result, the moving body 30a deforms or moves the valve body 50a so as to change from the first mode in which the flow path tubular member 40a does not pass through the valve body 50a and the opening 42 is closed by the valve body 50a to a mode (hereinafter referred to as a "second mode" as appropriate) in which the flow path tubular member 40a passes through the valve body 50a and the opening 42 is open from the valve body 50a while being kept in a state in which the female connector 2a is locked by the second female screw portion 37a, thereby forming a state illustrated in FIG. 5. At this time, since the flow path tubular member 40a passes through the valve body 50a and the elastic valve body 70 through the abutment region 73, the first flow path 41 and the second flow path 66 are made to communicate through the opening 42. Hereinafter, the connection state of the male connector 1a and the female connector 2a as illustrated in FIG. 5 will be described as the "second connection state".

On the other hand, when the female connector 2a is rotated counterclockwise with respect to the male connector 1a in the second connection state illustrated in FIG. 5, the moving body 30a changes the screwed state of the first male screw portion 35 with the first female screw portion 23 to move relative toward the distal end side with respect to the housing main body 20a together with the female connector 2a while being kept in a state in which the female connector 2a is locked by the second female screw portion 37a. As a result, the moving body 30a deforms or moves the valve body 50a so as to change from the second mode to the first mode. Further, the flow path tubular member 40a is removed from the elastic valve body 70 through the abutment region 73 by moving the moving body 30a so as to change from the second mode to the first mode. In the second embodiment, the valve body 50a is compressed by the movement of the moving body 30a toward the proximal end side and biases the moving body 30a to be in the first mode by a restoring force, and thus, it is possible to make a change from the second mode to the first mode with a weaker force than that in the case of making a change from the first mode to the second mode. When the concave portion 31 of the moving body 30a reaches the position of the convex portion 22 of the housing main body 20a, the convex portion 22 is fitted in the concave portion 31 to be displaced to the restriction position, thereby forming the first connection state illustrated in FIG. 4.

When the female connector 2a is further rotated counterclockwise with respect to the male connector 1a from the first connection state illustrated in FIG. 4, the female connector 2a moves relative to the distal end side with respect to the moving body 30a by screwing between the second male screw portion 65a of the female connector 2a and the second female screw portion 37a of the moving body 30a since the movement of the moving body 30a is restricted by the housing main body 20a via the convex portion 22. More specifically, the convex portion 22 is not pushed radially outward even by the moving body 30a that tries to advance toward the distal end side but continuously remains at the restriction position since the end surface on the proximal end side is substantially parallel to the radial direction as described above. At this time, the abutment between the bottom surface 72 of the elastic valve body 70 of the female connector 2a and the top surface 52 of the valve body 50a of the male connector 1a is released. That is, the abutment region 73 disappears. Then, the screwing between the second male screw portion 65a of the female connector 2a and the second female screw portion 37a of the moving body 30a is released, and the non-connection state as illustrated in FIG. 2 is formed by pulling the female connector 2a relative toward the distal end side with respect to the moving body 30a.

In this manner, the convex portion 22 serving as the second locking portion switches between the locking and unlocking of the moving body 30a, and thus, can change the mode between the first mode and the second mode. That is, the convex portion 22 forms a switching portion that can be displaced between the restriction position and the allowing position.

As described above, according to the male connector 1a of the present embodiment, the female connector 2a is locked by the male connector 1a in a state in which the valve body 50a of the male connector 1a and the elastic valve body 70 of the female connector 2a abut on each other to form the abutment region 73 by screwing between the second female screw portion 37a of the moving body 30a and the second male screw portion 65a of the second housing 60a when the flow path tubular member 40a of the male connector 1a is inserted into and removed from the elastic valve body 70 of the female connector 2a. The flow path tubular member 40a passes through the valve body 50a and the elastic valve body 70 through the abutment region 73. Accordingly, when the flow path tubular member 40a of the male connector 1a is inserted into and removed from the female connector 2a, the valve body 50a of the male connector 1a and the elastic valve body 70 of the female connector 2a abut on with each other, and thus, it is possible to inhibit a fluid from leaking out through the opening 42 of the flow path tubular member 40a of the male connector 1a.

Further, according to the male connector 1a of the present embodiment, it is possible to form the second connection state from the first connection state by continuously rotating the female connector 2a clockwise with respect to the male connector 1a when connecting the female connector 2a, and it is possible to remove the female connector 2a forming the first connection state from the second connection state by continuously rotating the female connector 2a counterclockwise with respect to the male connector 1a when removing the female connector 2a. Accordingly, the handling becomes easy since only one operation of rotating the female connector 2a in a predetermined direction (one rotation direction in this example) with respect to the male connector 1a is enough in order to connect or remove the female connector 2a to or from the male connector 1a.

Figure 6:
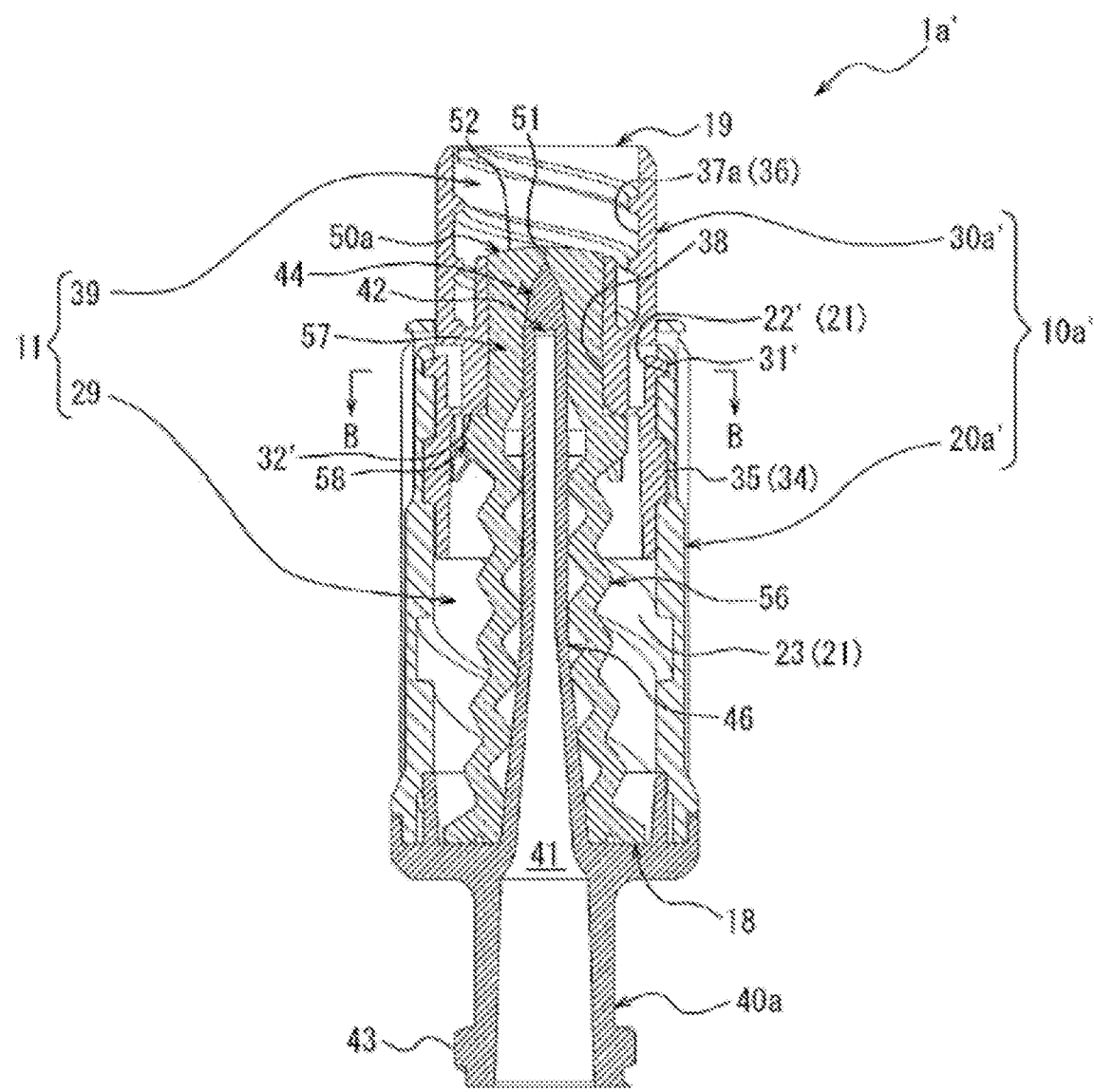
FIG. 6 is a cross-sectional view illustrating a modification of the male connector illustrated in FIG. 1.
Figure 7:
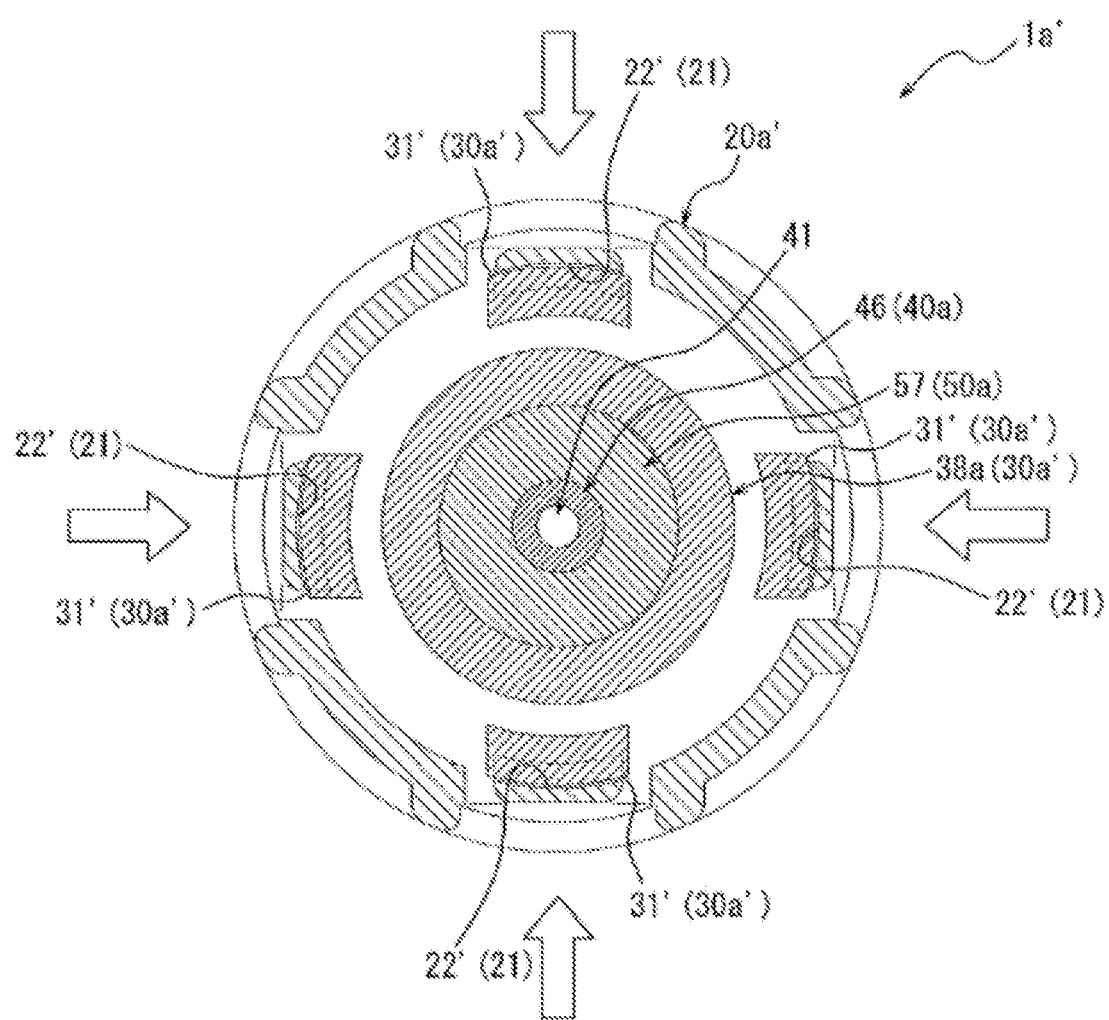
FIG. 7 is a cross-sectional view taken along line B-B of FIG. 6.

FIG. 6 is a cross-sectional view illustrating a male connector 1a' according to a modification of the male connector 1a according to the present embodiment, and FIG. 7 is a cross-sectional view taken along line B-B of FIG. 6. As illustrated in FIGS. 6 and 7, the male connector 1a' includes a first housing 10a', the flow path tubular member 40a, and the valve body 50a.

The first housing 10a' includes a housing main body 20a' and a moving body 30a' movable with respect to the housing main body 20a'. The housing main body 20a' is provided with a concave portion 22' on the inner peripheral wall 21 instead of the convex portion 22 of the housing main body 20a, and the other configurations thereof are the same as those of the housing main body 20a. The moving body 30a' is provided with a convex portion 31' on an outer peripheral wall between the proximal-end-side tubular portion 32 and the distal-end-side tubular portion 33 instead of the concave portion 31 of the moving body 30a, and the other configurations thereof are the same as those of the moving body 30a.

Even with the first housing 10a' configured in this manner, movement of the moving body 30a' with respect to the housing main body 20a' is restricted so as to maintain the first mode by arranging the convex portion 31' at a restriction position where the convex portion 31' is fitted and locked in the concave portion 22' as illustrated in FIG. 6, which is similar to the first housing 10a. Further, the convex portion 31' provided on the moving body 30a' of the first housing 10a' forms a switching portion that is displaceable between the restriction position to restrict the movement of the moving body 30a' with respect to the housing main body 20a' so as to maintain the first mode and an allowing position to allow the movement of the moving body 30a' with respect to the housing main body 20a' so as to change from the first mode to the second mode while being kept in a state in which the second female screw portion 37a serving as the first locking portion locks the female connector 2a, which is similar to the convex portion 22 provided on the housing main body 20a of the first housing 10a.

It may be configured such that the fitting state between the convex portion 31' and the concave portion 22' is released by rotating the female connector 2a clockwise with respect to the male connector 1a' when displacing the convex portion 31' from the restriction position to the allowing position similarly to the male connector 1a, but it may be configured such that the convex portion 31' is pressed from the outside so as to be displaced to the allowing position so as to release the fitting state with the concave portion 22', for example, as indicated by outlined arrows in FIG. 7.

Figure 8:
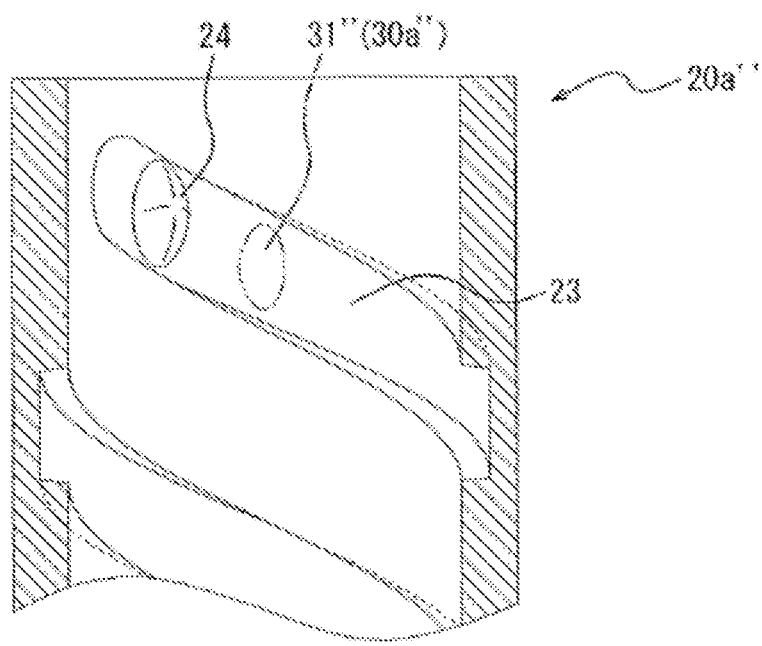
FIG. 8 is a cross-sectional view illustrating another modification of a housing main body of the male connector illustrated in FIG. 1.

FIG. 8 is a cross-sectional view illustrating a part of a housing main body 20a'' according to another modification of the housing main body 20a of the male connector 1a according to the present embodiment. As illustrated in FIG. 8, the housing main body 20a'' may be configured to include a protrusion 24 on a groove inner wall near an end portion on the distal end side of the first female screw portion 23 in addition to the convex portion 22 or instead of the convex portion 22. In such a case, a moving body 30a'' includes a protruding portion 31'' that slides and moves along a spiral groove of the first female screw portion 23 in addition to the concave portion 31 or instead of the concave portion 31. In FIG. 8, the protruding portion 31'' of the moving body 30a'' is indicated by a two-dot chain line for convenience of description. The protrusion 24 of the housing main body 20a'' forms a switching portion that is displaceable between a restriction position to restrict the movement of the moving body 30a'' so as to maintain the first mode by holding the protruding portion 31'' of the moving body 30a'' with the end portion of the distal end of the groove of the first female screw portion 23 and an allowing position to allow the movement of the moving body 30a'' so as to change from the first mode to the second mode by moving the protruding portion 31'' toward the proximal end side over the protrusion 24.

Second Embodiment

Figure 9:
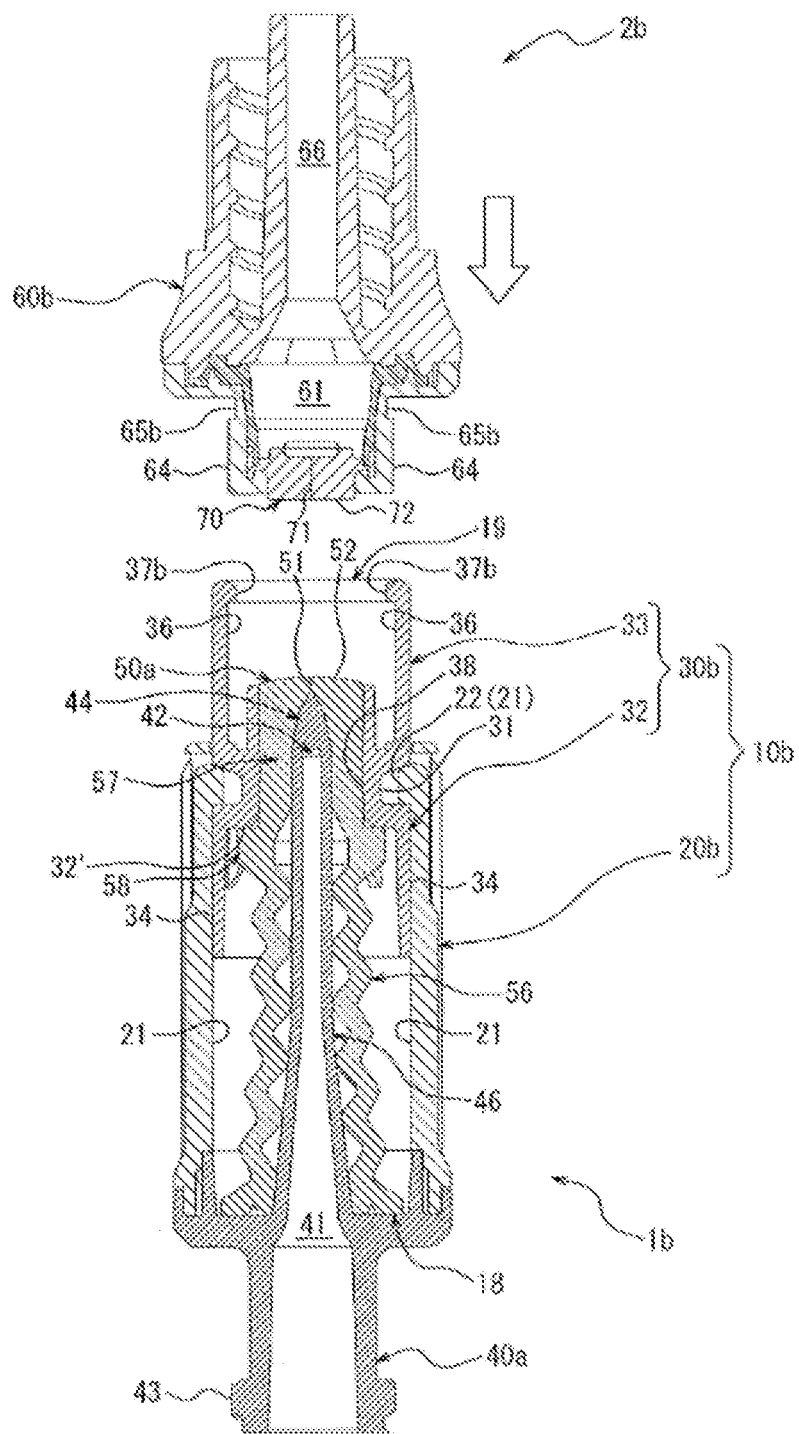
FIG. 9 is a cross-sectional view illustrating a male connector and a female connector according to a second embodiment.

FIG. 9 is a cross-sectional view illustrating a male connector 1b and a female connector 2b according to a second embodiment. The male connector 1b and the female connector 2b illustrated in FIG. 9 each illustrate a state of a single body before being connected to each other (non-connection state).

As illustrated in FIG. 9, the male connector 1b includes a first housing 10b, the flow path tubular member 40a, and the valve body 50a. The first housing 10b includes a housing main body 20b and a moving body 30b movable with respect to the housing main body 20b.

The housing main body 20b has the same configuration as the housing main body 20a of the first embodiment except that the first female screw portion 23 is not formed. The moving body 30b has the same configuration as the moving body 30a of the first embodiment except that the first male screw portion 35 and the second female screw portion 37a are not formed and a convex portion 37b is provided. The convex portion 37b is a claw-like protrusion protruding inward and provided at the distal end of the distal-end-side tubular portion 33 of the moving body 30b.

As illustrated in FIG. 9, the female connector 2b includes a second housing 60b and the elastic valve body 70. The second housing 60b has the same configuration as the second housing 60a of the first embodiment except that the second male screw portion 65a is not formed and a concave portion 65b is provided. The concave portion 65b is formed such that the convex portion 37b provided on the moving body 30b of the male connector 1b can be fitted thereinto.

Figure 10:
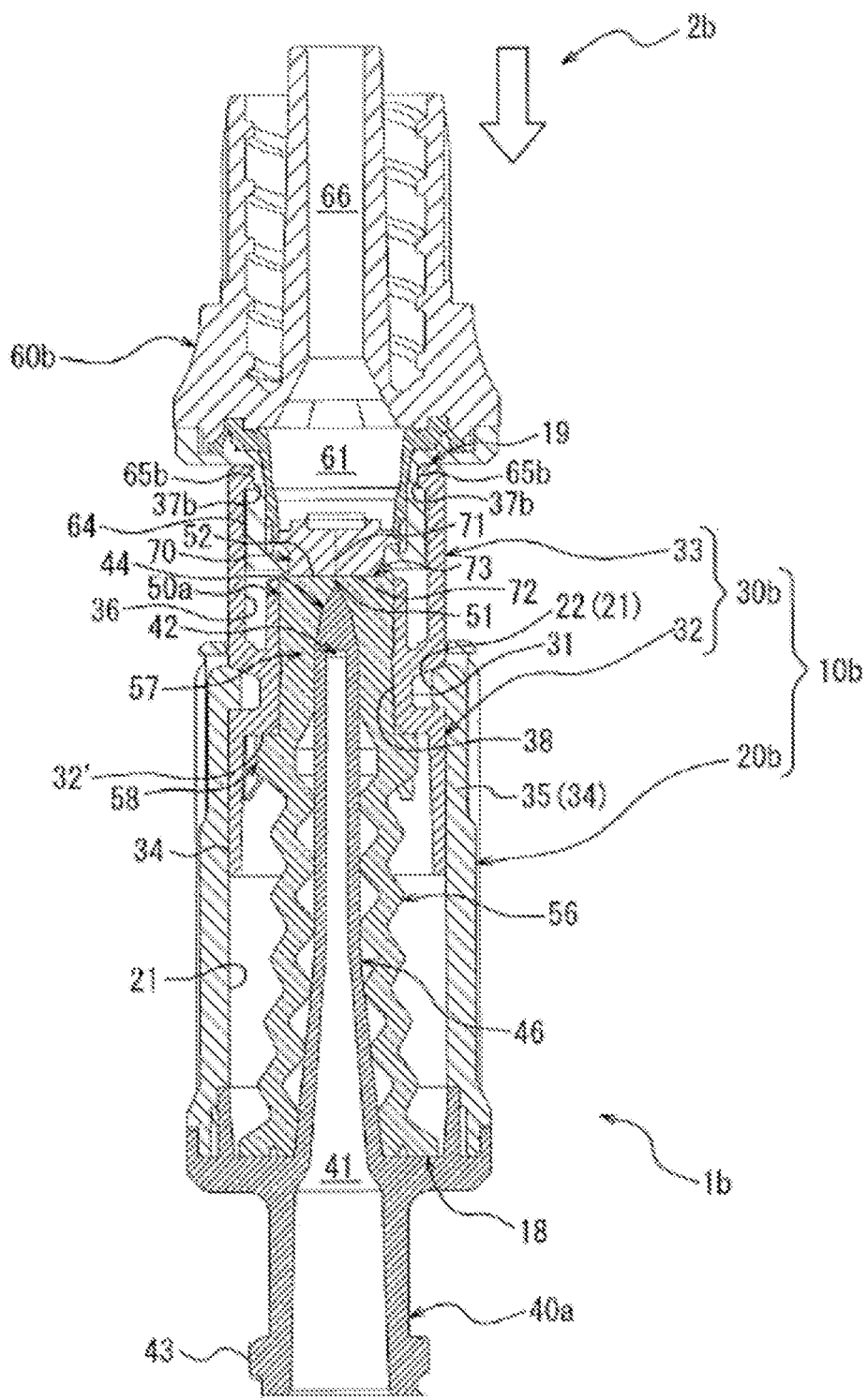
FIG. 10 is a cross-sectional view illustrating a first connection state of the male connector and the female connector illustrated in FIG. 9.
Figure 11:
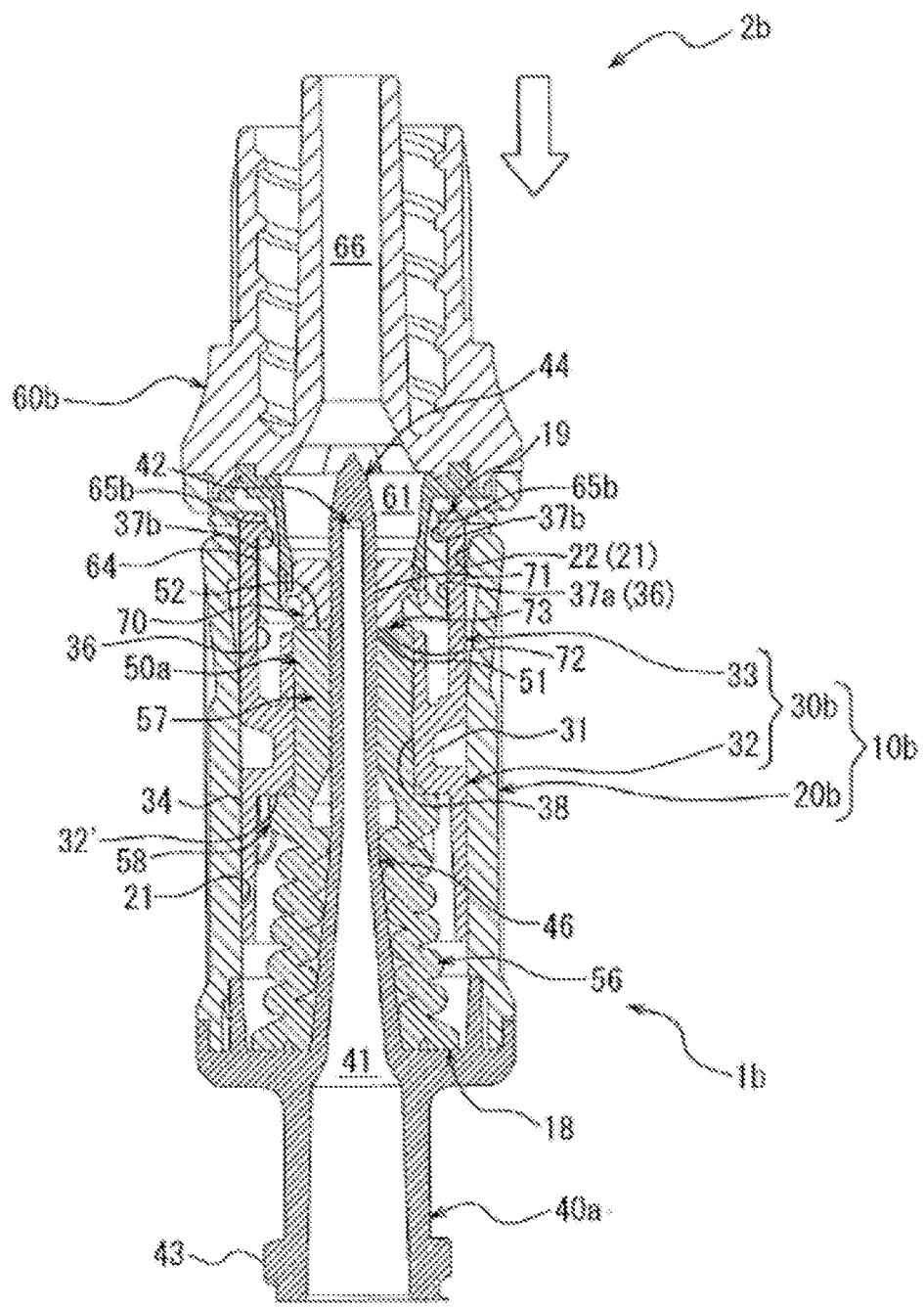
FIG. 11 is a cross-sectional view illustrating a second connection state of the male connector and the female connector illustrated in FIG. 9.

Hereinafter, a procedure of connecting the male connector 1b and the female connector 2b will be described with reference to FIGS. 9, 10, and 11. FIG. 10 is a cross-sectional view illustrating a first connection state of the male connector 1b and the female connector 2b according to the present embodiment, and FIG. 11 is a cross-sectional view illustrating a second connection state of the male connector 1b and the female connector 2b according to the present embodiment. The outlined arrows in FIGS. 9, 10, and 11 indicate a direction in which the female connector 2b is moved with respect to the male connector 1b when connecting the female connector 2b to the male connector 1b. The first connection state and the second connection state of the present embodiment mean the same connection states as the respective connection states of the first embodiment.

As illustrated in FIG. 9, in a state in which the convex portion 22 of the housing main body 20b is fitted and locked in the concave portion 31 of the moving body 30b, that is, in the state of being at a restriction position, the proximal end side of the female connector 2b is brought close to the distal end side of the male connector 1b with respect to the male connector 1b kept in the first mode so that the cap 62 of the female connector 2b is pushed into the distal-end-side tubular portion 33 of the moving body 30b. Then, the convex portion 37b provided in the distal-end-side tubular portion 33 of the moving body 30b is displaced in a diameter-enlarging direction by being pushed by the cap 62 of the female connector 2b, and the cap 62 is inserted into the hollow portion 39 of the distal-end-side tubular portion 33 and moved to the proximal end side. Then, as illustrated in FIG. 10, the bottom surface 72 of the elastic valve body 70 of the female connector 2b and the top surface 52 of the valve body 50a of the male connector 1b abut on each other to form the abutment region 73, and the convex portion 37b fits into the concave portion 65b and the female connector 2b is locked with respect to the male connector 1b. In other words, the convex portion 37b of the male connector 1b forms a first locking portion locking the female connector 2b by fitting with the concave portion 65b. At this time, the convex portion 22 serving as the second locking portion maintains the fitting state (locking state) with the concave portion 31 at the restriction position.

In the first connection state illustrated in FIG. 10, the female connector 2b is further pushed into the male connector 1b. Then, the fitting state between the convex portion 22 and the concave portion 31 is released since the moving body 30b tries to move toward the proximal end side with respect to the housing main body 20b together with the female connector 2b. In other words, the convex portion 22 serving as the second locking portion is displaced from the restriction position where the moving body 30b is locked to restrict movement to an allowing position where the locking of the moving body 30b is released to allow the movement while being kept in a state in which the convex portion 37b serving as the first locking portion locks the female connector 2b. Specifically, the convex portion 22 serving as the second locking portion of the present embodiment is displaced from the restriction position to the allowing position by moving radially outward, and is displaced from the allowing position to the restriction position by moving radially inward.

When the female connector 2b is further pushed into the male connector 1b after the convex portion 22 is displaced to the allowing position, the moving body 30b moves relative to the proximal end side with respect to the housing main body 20b together with the female connector 2b along the inner peripheral wall 21 of the housing main body 20b. As a result, the moving body 30b deforms or moves the valve body 50a so as to change from the first mode in which the flow path tubular member 40a does not pass through the valve body 50a and the opening 42 is closed by the valve body 50a to the second mode in which the flow path tubular member 40a passes through the valve body 50a and the opening 42 is open from the valve body 50a while being kept in a state in which the female connector 2b is locked by the convex portion 37b, thereby forming a state illustrated in FIG. 11. At this time, since the flow path tubular member 40a passes through the valve body 50a and the elastic valve body 70 through the abutment region 73, the first flow path 41 and the second flow path 66 are made to communicate through the opening 42.

On the other hand, in the second connection state illustrated in FIG. 11, when the female connector 2b is pulled toward the distal end side with respect to the male connector 1b, the moving body 30b moves relative toward the distal end side with respect to the housing main body 20b together with the female connector 2b along the inner peripheral wall 21 of the housing main body 20b while being kept in the state of locking the female connector 2b via the convex portion 37b. As a result, the moving body 30b deforms or moves the valve body 50a so as to change from the second mode to the first mode. In the second embodiment, the valve body 50a is compressed by the movement of the moving body 30b toward the proximal end side and biases the moving body 30b to be in the first mode by a restoring force, and thus, it is possible to make a change from the second mode to the first mode with a weaker force than that in the case of making a change from the first mode to the second mode. When the concave portion 31 of the moving body 30b reaches the position of the convex portion 22 of the housing main body 20b, the convex portion 22 is displaced to the restriction position so as to fit into the concave portion 31, thereby forming the first connection state illustrated in FIG. 10.

When the female connector 2b is further pulled toward the distal end side with respect to the male connector 1b from the first connection state illustrated in FIG. 10, the fitting state between the concave portion 65b of the female connector 2b and the convex portion 37b of the moving body 30b is released since the movement of the moving body 30b is restricted by the housing main body 20b via the convex portion 22, and the female connector 2b moves relative to the distal end side with respect to the male connector 1b. At this time, the abutment between the bottom surface 72 of the elastic valve body 70 of the female connector 2b and the top surface 52 of the valve body 50a of the male connector 1b is released. Then, the non-connection state as illustrated in FIG. 9 is formed by pulling the female connector 2b toward the distal end side.

In this manner, the convex portion 22 serving as the second locking portion switches between the locking and unlocking of the moving body 30b, and thus, can change the mode between the first mode and the second mode. That is, the convex portion 22 forms a switching portion that can be displaced between the restriction position and the allowing position.

As described above, according to the male connector 1b of the present embodiment, when the flow path tubular member 40a of the male connector 1b is inserted into and removed from the elastic valve body 70 of the female connector 2b, the flow path tubular member 40a locked by the male connector 1b penetrates the valve body 50a and the elastic valve body 70 through the abutment region 73 in a state in which the valve body 50a of the male connector 1b and the elastic valve body 70 of the female connector 2b abut on each other to form the abutment region 73 by fitting between the convex portion 37b of the moving body 30b and the concave portion 65b of the second housing 60b. Accordingly, when the flow path tubular member 40a of the male connector 1b is inserted into and removed from the female connector 2b, the valve body 50a of the male connector 1b and the elastic valve body 70 of the female connector 2b abut on with each other, and thus, it is possible to inhibit a fluid from leaking out through the opening 42 of the flow path tubular member 40a of the male connector 1b.

Further, according to the male connector 1b of the present embodiment, it is possible to form the second connection state from the first connection state by continuously pushing the female connector 2b relative toward the proximal end side with respect to the male connector 1b when connecting the female connector 2b, and it is possible to remove the female connector 2b by forming the first connection state from the second connection state by continuously pulling the female connector 2b relative toward the distal end side with respect to the male connector 1b when removing the female connector 2b. Accordingly, the handling becomes easy since only one operation of biasing the female connector 2b in a direction in which the female connector 2b is desirably moved with respect to the male connector 1b (in this example, in a straight line direction) is enough in order to connect or remove the female connector 2b to or from the male connector 1b.

Third Embodiment

Figure 12:
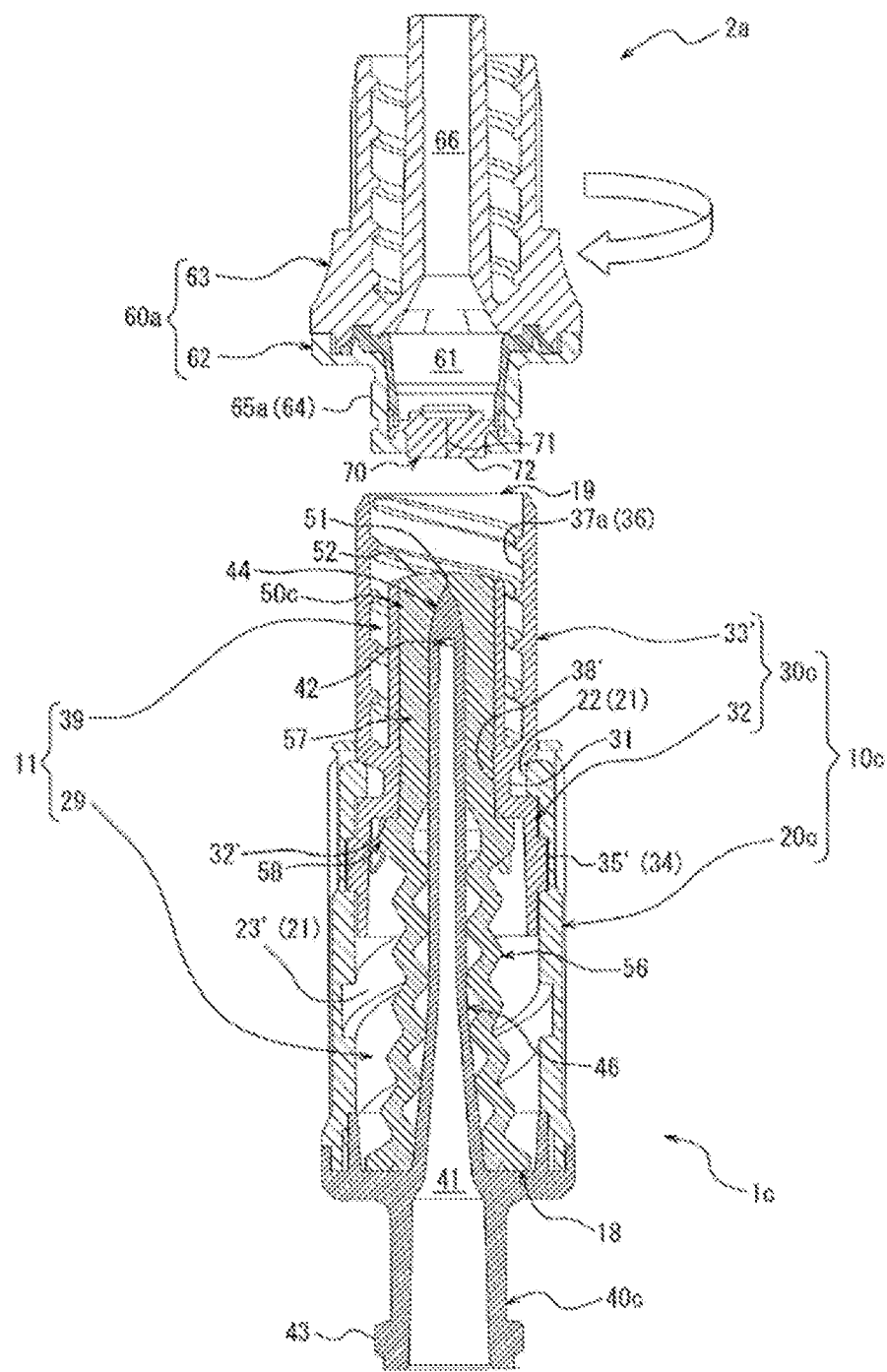
FIG. 12 is a cross-sectional view illustrating a male connector and a female connector according to a third embodiment.

FIG. 12 is a cross-sectional view illustrating a male connector 1c and the female connector 2a according to a third embodiment. The male connector 1c and the female connector 2a illustrated in FIG. 12 each illustrate a state of a single body before being connected to each other (non-connection state).

As illustrated in FIG. 12, the male connector 1c includes a first housing 10c, a flow path tubular member 40c, and a valve body 50c. The first housing 10c includes a housing main body 20c and a moving body 30c movable with respect to the housing main body 20c.

The housing main body 20c has the same configuration as the housing main body 20a of the first embodiment except that a first female screw portion 23' having a reverse screw relationship with the first female screw portion 23 is provided instead of the first female screw portion 23. The moving body 30c has the same configuration as the moving body 30a of the first embodiment except that a first male screw portion 35' having a reverse screw relationship with the first male screw portion 35 is provided instead of the first male screw portion 35, and a distal-end-side tubular portion 33' and a valve body holding portion 38' that is longer on the distal end side are provided instead of the distal-end-side tubular portion 33 and the valve body holding portion 38.

The flow path tubular member 40c has the same configuration as the flow path tubular member 40a of the first embodiment except that the flow path tubular member 40c is longer on the distal end side. The valve body 50c has the same configuration as the valve body 50a of the first embodiment except that the valve body 50c is longer on the distal end side.

Figure 13:
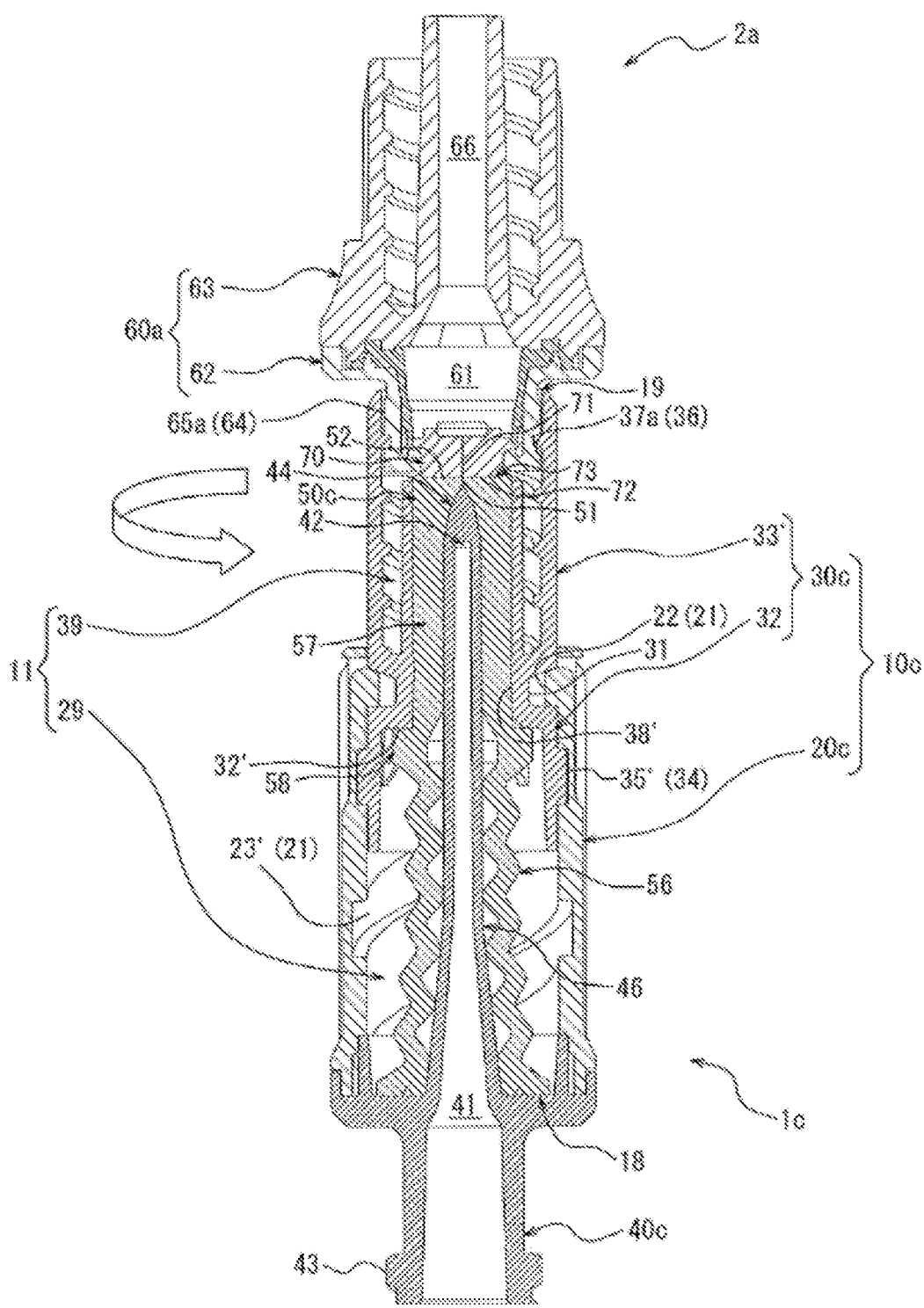
FIG. 13 is a cross-sectional view illustrating a first connection state of the male connector and the female connector illustrated in FIG. 12.
Figure 14:
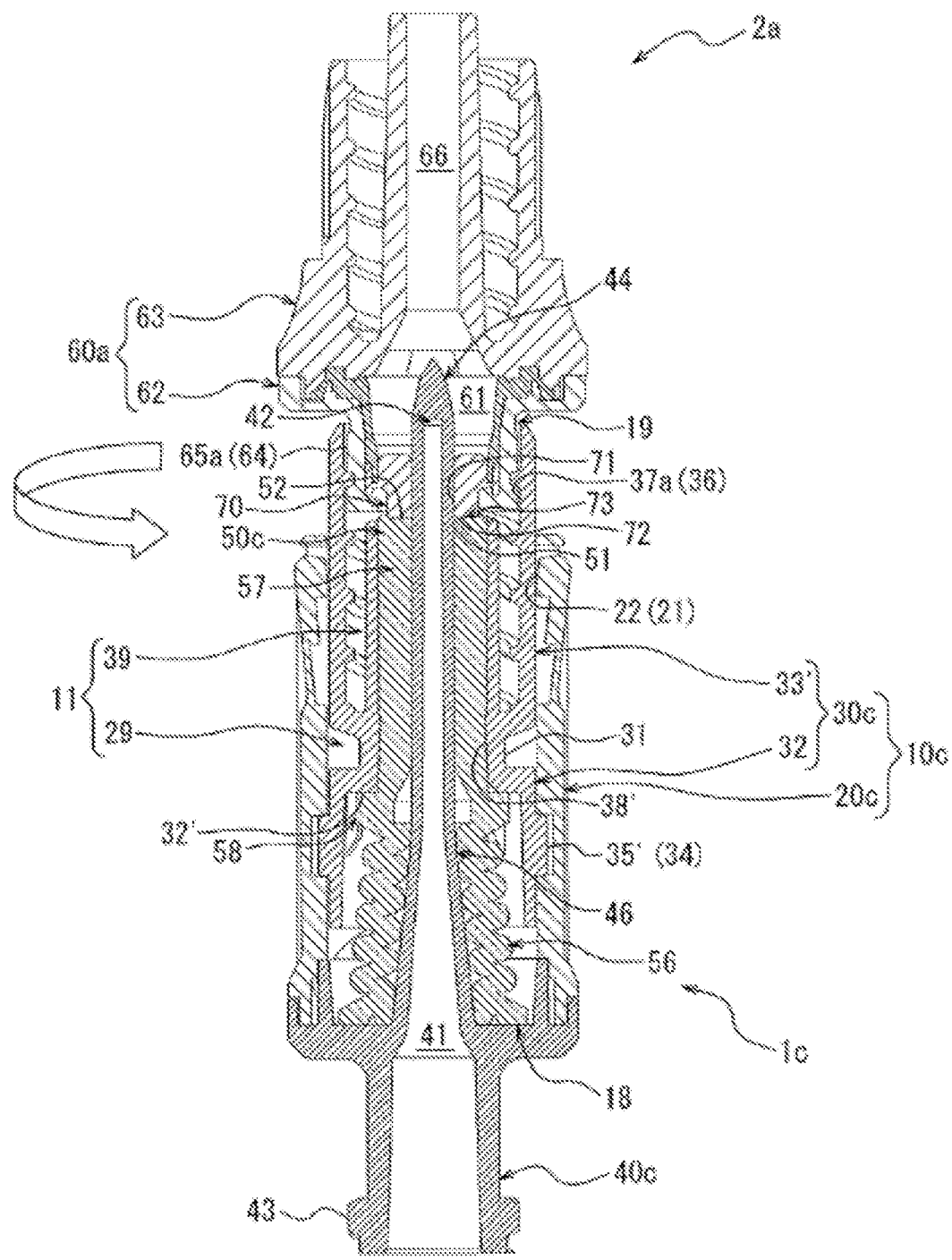
FIG. 14 is a cross-sectional view illustrating a second connection state of the male connector and the female connector illustrated in FIG. 12.

Hereinafter, a procedure of connecting the male connector 1c and the female connector 2a will be described with reference to FIGS. 12, 13, and 14. FIG. 13 is a cross-sectional view illustrating a first connection state of the male connector 1c and the female connector 2a according to the present embodiment, and FIG. 14 is a cross-sectional view illustrating the second connection state of the male connector 1c and the female connector 2a according to the present embodiment. The outlined arrows in FIGS. 12, 13, and 14 indicate a direction in which the female connector 2a is rotated with respect to the male connector 1c when connecting the female connector 2a to the male connector 1c. The first connection state and the second connection state of the present embodiment mean the same connection states as the respective connection states of the first embodiment.

As illustrated in FIG. 12, in a state in which the convex portion 22 of the housing main body 20c is fitted and locked in the concave portion 31 of the moving body 30c, that is, in the state of being at a restriction position, the female connector 2a is rotated clockwise with respect to the male connector 1c while bringing the proximal end side of the female connector 2a close to the distal end side of the male connector 1c with respect to the male connector 1c kept in the first mode. Then, the second male screw portion 65a of the female connector 2a and the second female screw portion 37a of the male connector 1c are screwed with each other so that the female connector 2a moves relative to the proximal end side with respect to the male connector 1c, and the bottom surface 72 of the elastic valve body 70 of the female connector 2a abuts on the top surface 52 of the valve body 50a of the male connector 1c to form an abutment region 73, as illustrated in FIG. 13. At this time, the second male screw portion 65a of the female connector 2a and the second female screw portion 37a of the male connector 1c are screwed with each other so that the female connector 2a is locked with respect to the male connector 1c. In other words, the second female screw portion 37a of the male connector 1c is screwed with the second male screw portion 65a to form the first locking portion locking the female connector 2a while maintaining the abutment region 73. At this time, the convex portion 22 serving as the second locking portion maintains the fitting state (locking state) with the concave portion 31 at the restriction position.

In the first connection state illustrated in FIG. 13, for example, the moving body 30c is grasped to rotate the moving body 30c counterclockwise with respect to the housing main body 20c. Then, the fitting state between the convex portion 22 and the concave portion 31 is released since the moving body 30c tries to rotate counterclockwise with respect to the housing main body 20c together with the female connector 2a. In other words, the convex portion 22 serving as the second locking portion is displaced from the restriction position to restrict the movement by locking the moving body 30c to an allowing position where the locking of the moving body 30c is released to allow the movement, while being kept in a state in which the second female screw portion 37a serving as the first locking portion locks the female connector 2a.

When the moving body 30c is further rotated counterclockwise with respect to the housing main body 20c after the convex portion 22 is displaced to the allowing position, the moving body 30c moves relative to the proximal end side with respect to the housing main body 20c together with the female connector 2a by changing the screwing state between the first male screw portion 35' and the first female screw portion 23'. As a result, the moving body 30c deforms or moves the valve body 50c so as to change from the first mode in which the flow path tubular member 40c does not pass through the valve body 50c and the opening 42 is closed by the valve body 50c to a mode (hereinafter referred to as a "second mode" as appropriate) in which the flow path tubular member 40c passes through the valve body 50c and the opening 42 is open from the valve body 50c while being kept in a state in which the female connector 2a is locked by the second female screw portion 37a, thereby forming a state illustrated in FIG. 14. At this time, since the flow path tubular member 40c passes through the valve body 50c and the elastic valve body 70 through the abutment region 73, the first flow path 41 and the second flow path 66 are made to communicate through the opening 42.

On the other hand, when the moving body 30c is rotated clockwise with respect to the housing main body 20c in the second connection state illustrated in FIG. 14, the moving body 30c changes the screwed state of the first male screw portion 35' with the first female screw portion 23' to move relative toward the distal end side with respect to the housing main body 20c together with the female connector 2a while being kept in a state in which the female connector 2a is locked by the second female screw portion 37a. As a result, the moving body 30c deforms or moves the valve body 50c so as to change from the second mode to the first mode. In the second embodiment, the valve body 50c is compressed by the movement of the moving body 30c toward the proximal end side and biases the moving body 30c to be in the first mode by a restoring force, and thus, it is possible to make a change from the second mode to the first mode with a weaker force than that in the case of making a change from the first mode to the second mode. When the concave portion 31 of the moving body 30c reaches the position of the convex portion 22 of the housing main body 20c, the convex portion 22 is fitted in the concave portion 31 to be displaced to the restriction position, thereby forming the first connection state illustrated in FIG. 13.

When the female connector 2a is rotated counterclockwise with respect to the male connector 1c from the first connection state illustrated in FIG. 13, the female connector 2a moves relative to the distal end side with respect to the male connector 1c by screwing between the second male screw portion 65a of the female connector 2a and the second female screw portion 37a of the moving body 30c since the movement of the moving body 30c is restricted by the housing main body 20c via the convex portion 22. At this time, the abutment between the bottom surface 72 of the elastic valve body 70 of the female connector 2a and the top surface 52 of the valve body 50c of the male connector 1c is released. Then, the screwing between the second male screw portion 65a of the female connector 2a and the second female screw portion 37a of the moving body 30c is released, and the non-connection state as illustrated in FIG. 12 is formed by pulling the female connector 2a toward the distal end side.

In this manner, the convex portion 22 serving as the second locking portion switches between the locking and unlocking of the moving body 30c, and thus, can change the mode between the first mode and the second mode. That is, the convex portion 22 forms a switching portion that can be displaced between the restriction position and the allowing position.

As described above, according to the male connector 1c of the present embodiment, the female connector 2a is locked by the male connector 1c in a state in which the valve body 50c of the male connector 1c and the elastic valve body 70 of the female connector 2a abut on each other to form the abutment region 73 by screwing between the second female screw portion 37a of the moving body 30c and the second male screw portion 65a of the second housing 60a when the flow path tubular member 40c of the male connector 1c is inserted into and removed from the elastic valve body 70 of the female connector 2a. The flow path tubular member 40c passes through the valve body 50c and the elastic valve body 70 through the abutment region 73. Accordingly, when the flow path tubular member 40c of the male connector 1c is inserted into and removed from the female connector 2a, the valve body 50c of the male connector 1c and the elastic valve body 70 of the female connector 2a abut on with each other, and thus, it is possible to inhibit a fluid from leaking out through the opening 42 of the flow path tubular member 40c of the male connector 1c.

Fourth Embodiment

Figure 15:
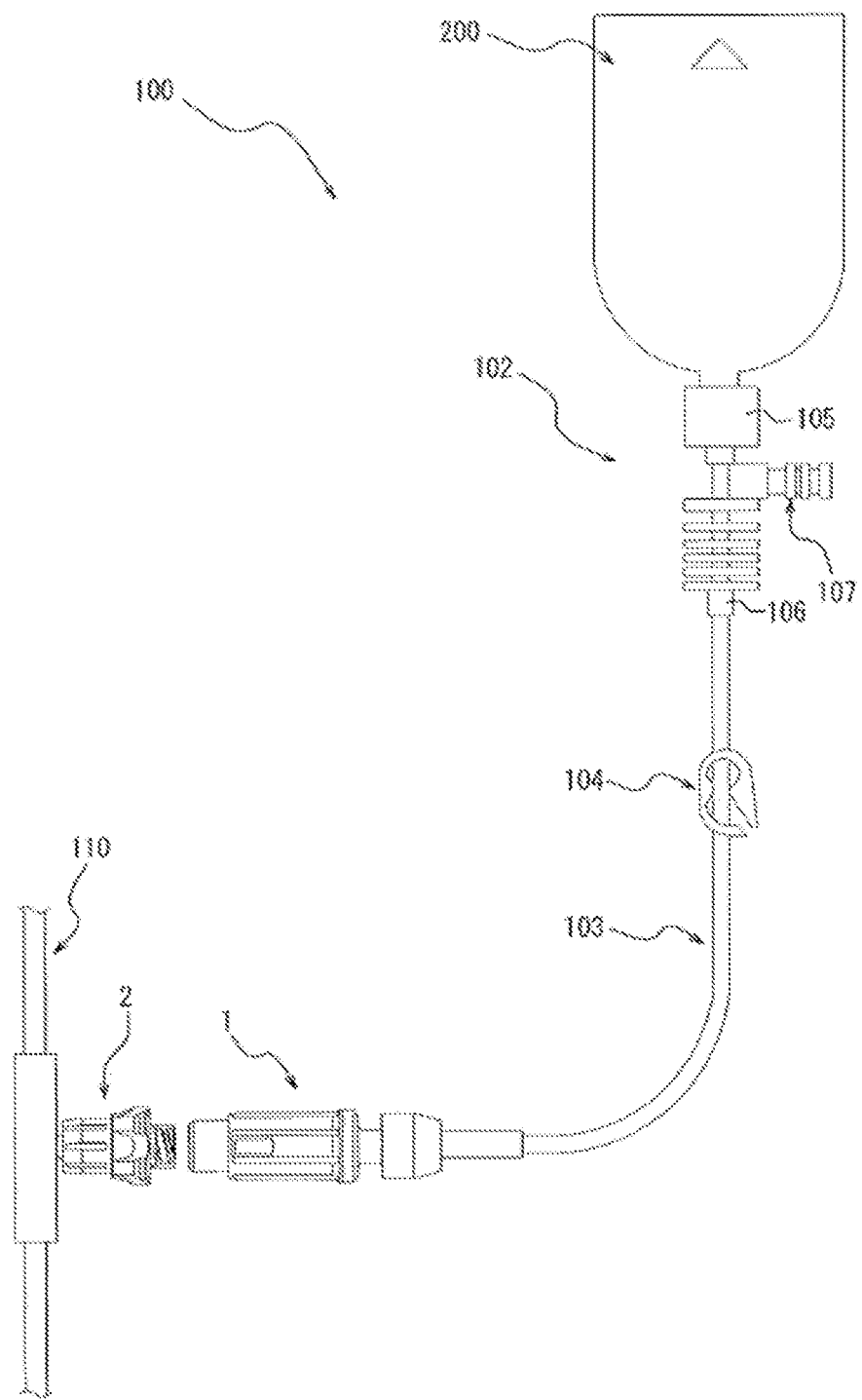
FIG. 15 is a view illustrating an infusion tube set (medical device) having the male connector illustrated in FIG. 1 as a fourth embodiment.

Finally, an infusion tube set 100 as a medical device including the above-described male connector 1a, 1a', 1b, or 1c (hereinafter collectively referred to as a "male connector 1") will be described. FIG. 15 is a view illustrating a state in which the infusion tube set 100 including the male connector 1, which is a fourth embodiment, is connected to another infusion tube set 110 including the above-described female connector 2a or 2b (hereinafter collectively referred to as a "female connector 2"). The infusion tube set 100 and the other infusion tube set 110 are used to administer an infusion solution such as a medicinal solution to a living body. As illustrated in FIG. 15, the infusion tube set 100 includes a connection device 102 connected to a medicinal solution container 200, the male connector 1 positioned on the downstream side (the distal end side) of the connection device 102, and a medical tube 103 connecting the connection device 102 and the male connector 1. Further, a clamp 104 may be mounted in the middle of the medical tube 103 so as to close the part. The clamp 104 is configured to press the medical tube 103 so as to clamp the medical tube 103 from the outside, thereby pressing and closing the inside of the medical tube 103.

In the infusion tube set 100 having such a configuration, a liquid such as a medicinal solution in the medicinal solution container 200 flows from the connection device 102 into the male connector 1 through the medical tube 103 in a state in which the clamp 104 is removed. Then, for example, when the male connector 1 is connected to the other infusion tube set 110 having the above-described female connector 2 as a mixed injection port via the female connector 2, the liquid flowing into the male connector 1 passes through each inside of the male connector 1 and the female connector 2 to flow into the other infusion tube set 110, thereby being supplied to the living body.

The connection device 102 includes a first connection portion 105 positioned at a proximal end portion and connected to the medicinal solution container 200, a second connection portion 106 positioned at a distal end portion and connected to the medical tube 103, and a third connection portion 107 provided so as to protrude toward the lateral side from an outer wall and to which a syringe is connected. In the connection device 102, a main flow path that communicates from the first connection portion 105 to the second connection portion 106 and is capable of transporting the liquid in the medicinal solution container 200 to the medical tube 103, and a sub flow path that communicates between the first connection portion 105 and the third connection portion 107 and that is capable of transporting a liquid between the medicinal solution container 200 and the syringe connected to the third connection portion 107 are defined.

Therefore, the medicinal solution in the syringe can be transported to the medicinal solution container 200 via the sub flow path of the connection device 102 by connecting the syringe containing a medicinal solution, which contains, for example, an anticancer agent, therein to the third connection portion 107 of the connection device 102. Then, the medicinal solution containing the anticancer agent contained in the medicinal solution container 200 is supplied to the male connector 1 through the main flow path of the connection device 102 and the inside of the medical tube 103.

As described above, the female connector 2 is connected to the distal end side of the male connector 1, and the medicinal solution containing the anticancer agent is supplied into the other infusion tube set 110, whereby the medicinal solution containing the anticancer agent can be administered to the living body. Further, the valve body 50a or 50c of the male connector 1 is closed when the medicinal solution administration is completed and the connection between the male connector 1 and the female connector 2 is released so that the medicinal solution containing the anticancer agent is inhibited from leaking out from the distal end of the male connector 1.

Although the infusion tube set 100 is exemplified as the medical device having the male connector 1, the male connector 1 is not limited to the infusion tube set, and can be used for other medical devices. For example, a syringe having the male connector 1 at a distal end portion of a syringe main body may be used. In such a case, for example, the third connection portion 107 of the above-described connection tool 102 may have the same configuration as the female connector 2, and the syringe having the male connector 1 may be connected to the third connection portion 107.

The male connector, the medical device including the male connector, and the method of connecting the male connector and the female connector according to the present disclosure are not limited to those of the above-described embodiments, and can be realized by various configurations within a range not departing from the contents described in the claims. For example, the valve body 50a or 50c does not necessarily cover one end on the distal end side of the flow path tubular member 40a or 40c, and may be configured to close the opening 42 of the flow path tubular member 40a or 40c in the first mode and open the opening 42 of the flow path tubular member 40a or 40c in the second mode.

Further, the slit 51 of the valve body 50a or 50c and the slit 71 of the elastic valve body 70 are not necessarily provided in advance, and may be configured to communicate by being pierced by the flow path tubular member 40a or 40c.

Further, the end surface on the proximal end side of the convex portion 22 does not need to be substantially parallel to the radial direction, and may be configured to continuously remain at the restriction position without being pushed radially outward even by the moving body 30a that tries to advance toward the distal end side. For example, the end surface on the proximal end side of the convex portion 22 may be inclined so as to be directed toward the proximal end side in the radially inward direction.

REFERENCE SIGNS LIST 1, 1a, 1a', 1b, 1c male connector
2, 2a, 2b female connector
10a, 10a', 10b, 10c first housing
11 hollow portion of first housing
18 proximal end of first housing
19 distal end of first housing
20a, 20a', 20a", 20b, 20c housing main body
21 inner peripheral wall
22 convex portion
22' concave portion
23, 23' first female screw portion
24 protrusion
29 hollow portion
30a, 30a', 30a", 30b, 30c moving body
31 concave portion
31' convex portion
31" protruding portion
32 proximal-end-side tubular portion
32' stepped surface
33, 33' distal-end-side tubular portion
34 proximal-end-side outer peripheral wall
35, 35' first male screw portion
36 distal-end-side inner peripheral wall
37a second female screw portion
37b convex portion
38, 38' valve body holding portion
39 hollow portion
40a, 40c flow path tubular member
41 first flow path
42 opening
43 medical device connection portion
44 tip portion
46 flow path tube main body
50a, 50c valve body
51 slit of valve body
52 top surface of valve body
56 bellows-cylindrical portion
56 tip portion
57 annular flange portion
60a, 60b second housing
61 male connector insertion portion
62 cap
63 holder
64 outer peripheral wall of cap
65a second male screw portion
65b concave portion
66 second flow path
70 elastic valve body
71 slit of elastic valve body
72 bottom surface of elastic valve body
73 abutment region
100 infusion tube set (medical device)
102 connection device
103 medical tube
104 clamp
105 first connection portion
106 second connection portion
107 third connection portion
110 another infusion tube set
200 medicinal solution container

What is claimed is:

1. A male connector that is connectable to a female connector that comprises an elastic valve body, the male connector comprising:
   a housing that defines a hollow portion;
   a tubular member that extends inside the hollow portion and has an opening at an end portion in an extending direction; and
   a valve body that is positioned inside the hollow portion and closes the opening of the tubular member,
   wherein the valve body comprises:
      a distal end portion, and
      a deformable portion,
   wherein the housing comprises:
      a housing main body, and
      a moving body comprising:
         a tubular valve body holding portion that holds the distal end portion of the valve body such that the distal end portion of the valve body moves along with movement of the tubular valve body holding portion, and
         a distal-end-side tubular portion extending distally from the tubular valve body holding portion and comprising a locking portion configured to lock the female connector in a state in which the valve body and the elastic valve body of the female connector abut on each other to form an abutment region;
   wherein the moving body is configured to move with respect to the housing main body, and movement of the tubular valve body holding portion causes movement of the distal end portion of the valve body and deformation of the deformable portion of the valve body, so as to change a mode between (i) a first mode in which the opening of the tubular member is closed by the valve body, and a distal end of the distal-end-side tubular portion extends past a distal end of the housing main body, and (ii) a second mode in which the opening of the tubular member is open from the valve body,
   wherein at least one of the housing main body and the moving body comprises a switching portion that is displaceable between (i) a restriction position in which movement of the other of the housing main body and the moving body is restricted so as to maintain the first mode, and (ii) an allowing position in which movement of said other of the housing main body and the moving body is allowed so as to change from the first mode to the second mode while maintaining a state in which the locking portion locks the female connector.

2. The male connector according to claim 1, wherein:
   the locking portion is a first locking portion, and
   the switching portion includes a second locking portion configured to lock said other of the housing main body and the moving body at the restriction position such that the mode is changeable between the first mode and the second mode by switching between locking and unlocking of said other of the housing main body and the moving body using the second locking portion.

3. The male connector according to claim 2, wherein the second locking portion includes a convex portion that fits in a concave portion provided on said other of the housing main body and the moving body.

4. The male connector according to claim 2, wherein:
   a female screw portion is formed on an inner peripheral wall of the housing main body, and
   the moving body is configured to move with respect to the housing main body as a male screw portion formed on an outer peripheral wall of the moving body is screwed with the female screw portion.

5. The male connector according to claim 4, wherein:
the male screw portion is a first male screw portion,
the female screw portion is a first female screw portion,
a second female screw portion is formed on an inner peripheral wall of the moving body,
a second male screw portion is formed on an outer peripheral wall of the female connector, the second male screw portion being screwable with the second female screw portion, and
the first locking portion includes the second female screw portion.

6. The male connector according to claim 5, wherein a direction in which the moving body moves by screwing between the first male screw portion and the first female screw portion as the moving body rotates in a predetermined direction with respect to the housing main body is identical to a direction in which the female connector moves by screwing between the second male screw portion and the second female screw portion as the female connector rotates in the predetermined direction with respect to the moving body.

7. The male connector according to claim 1, wherein the valve body biases the moving body in the second mode to be in the first mode.

8. The male connector according to claim 1, wherein:
the valve body covers the end portion including the opening of the tubular member, and
the tubular member does not pass through the valve body in the first mode, and the tubular member passes through the valve body in the second mode.

9. A male connector that is connectable to a female connector that comprises an elastic valve body, the male connector comprising:
a housing that defines a hollow portion;
a tubular member that extends inside the hollow portion and has an opening at an end portion in an extending direction; and
a valve body that is positioned inside the hollow portion and closes the opening of the tubular member,
wherein the valve body comprises:
a distal end portion, and
a deformable portion,
wherein the housing comprises:
a housing main body, and
a moving body comprising:
a tubular valve body holding portion that holds the distal end portion of the valve body such that the distal end portion of the valve body moves along with movement of the tubular valve body holding portion, and
a distal-end-side tubular portion extending distally from the tubular valve body holding portion and comprising a locking portion configured to lock the female connector in a state in which the valve body and the elastic valve body of the female connector abut on each other to form an abutment region;
wherein the moving body is configured to move with respect to the housing main body, and movement of the tubular valve body holding portion causes movement of the distal end portion of the valve body and deformation of the deformable portion of the valve body, so as to change a mode between (i) a first mode in which the opening of the tubular member is closed by the valve body, (ii) and a second mode in which the opening of the tubular member is open from the valve body, and
wherein the moving body is configured to move so as to change from the first mode to the second mode in a state in which the valve body and the elastic valve body of the female connector abut on each other to form the abutment region in the first mode so that the tubular member is caused to pass through the valve body and the elastic valve body through the abutment region.

10. The male connector according to claim 9, wherein, when the moving body is in the first mode, a distal end of the distal-end-side tubular portion extends past a distal end of the housing main body.

11. A male connector that is connectable to a female connector that comprises an elastic valve body, the male connector comprising:
a housing that defines a hollow portion;
a tubular member that extends inside the hollow portion and has an opening at an end portion in an extending direction; and
a valve body that is positioned inside the hollow portion and closes the opening of the tubular member,
wherein the valve body comprises:
a distal end portion, and
a deformable portion,
wherein the housing comprises:
a housing main body, and
a moving body comprising:
a tubular valve body holding portion that holds the distal end portion of the valve body such that the distal end portion of the valve body moves along with movement of the tubular valve body holding portion, and
a distal-end-side tubular portion extending distally from the tubular valve body holding portion and comprising a locking portion configured to lock the female connector in a state in which the valve body and the elastic valve body of the female connector abut on each other to form an abutment region;
wherein the moving body is configured to move with respect to the housing main body, and movement of the tubular valve body holding portion causes movement of the distal end portion of the valve body and deformation of the deformable portion of the valve body, so as to change a mode between (i) a first mode in which the opening of the tubular member is closed by the valve body, and (ii) a second mode in which the opening of the tubular member is open from the valve body, and
wherein the moving body is configured to move so as to change from the second mode to the first mode in a state in which the valve body and the elastic valve body of the female connector abut on each other to form the abutment region in the second mode so that the tubular member is caused to be removed from the elastic valve body through the abutment region.

12. The male connector according to claim 11, wherein, when the moving body is in the first mode, a distal end of the distal-end-side tubular portion extends past a distal end of the housing main body.

13. A method for connecting a female connector and a male connector, the method comprising:
providing a female connector comprising an elastic valve body, providing a male connector comprising:
- a housing that defines a hollow portion,
- a tubular member that extends inside the hollow portion and has an opening at an end portion in an extending direction, and
- a valve body that is positioned inside the hollow portion and closes the opening of the tubular member,
- wherein the valve body comprises:
  - a distal end portion, and
  - a deformable portion,
- wherein the housing comprises:
  - a housing main body, and
  - a moving body comprising:
    - a tubular valve body holding portion that holds the distal end portion of the valve body such that the distal end portion of the valve body moves along with movement of the tubular valve body holding portion, and
    - a distal-end-side tubular portion extending distally from the tubular valve body holding portion and comprising a locking portion configured to lock the female connector in a state in which the valve body and the elastic valve body of the female connector abut on each other to form an abutment region;
- wherein the moving body is configured to move with respect to the housing main body, and movement of the tubular valve body holding portion causes movement of the distal end portion of the valve body and deformation of the deformable portion of the valve body, so as to change a mode between (i) a first mode in which the opening of the tubular member is closed by the valve body, and a distal end of the distal-end-side tubular portion extends past a distal end of the housing main body, and (ii) a second mode in which the opening of the tubular member is open from the valve body;
- locking the female connector by the moving body in a state in which the valve body and the elastic valve body of the female connector abut on each other to form the abutment region in the first mode; and
- moving the moving body so as to change from the first mode to the second mode in a state in which the female connector is locked by the moving body so that the tubular member is caused to pass through the valve body and the elastic valve body through the abutment region.

14. A male connector that is connectable to a female connector that comprises an elastic valve body, the male connector comprising:
- a housing that defines a hollow portion;
- a tubular member that extends inside the hollow portion and has an opening at an end portion in an extending direction; and
- a valve body that is positioned inside the hollow portion and that closes the opening of the tubular member,
- wherein the valve body comprises:
  - a distal end portion, and
  - a deformable portion,
- wherein the housing comprises:
  - a housing main body, and
  - a moving body comprising:
    - a tubular valve body holding portion that holds the distal end portion of the valve body such that the distal end portion of the valve body moves along with movement of the tubular valve body holding portion, and
    - a distal-end-side tubular portion extending distally from the tubular valve body holding portion and comprising a locking portion configured to lock the female connector in a state in which the valve body and the elastic valve body of the female connector abut on each other to form an abutment region;
- wherein the moving body is configured to move with respect to the housing main body, and movement of the tubular valve body holding portion causes movement of the distal end portion of the valve body and deformation of the deformable portion of the valve body, so as to change a mode between (i) a first mode in which the opening of the tubular member is closed by the valve body, and a distal end of the distal-end-side tubular portion extends past a distal end of the housing main body, and (ii) a second mode in which the opening of the tubular member is open from the valve body,
- wherein at least one of the housing main body and the moving body is configured to restricting movement of the other of the housing main body and the moving body so as to maintain the first mode while maintaining a state in which the locking portion locks the female connector.

* * * * *